US011872242B2

(12) United States Patent
Hazan

(10) Patent No.: US 11,872,242 B2
(45) Date of Patent: *Jan. 16, 2024

(54) METHODS OF PREVENTING AND TREATING COVID-19 INFECTION

(71) Applicant: Sabine Hazan, Ventura, CA (US)

(72) Inventor: Sabine Hazan, Ventura, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/350,520

(22) Filed: Jun. 17, 2021

(65) Prior Publication Data

US 2021/0308167 A1    Oct. 7, 2021

Related U.S. Application Data

(60) Continuation of application No. 17/126,715, filed on Dec. 18, 2020, now Pat. No. 11,166,971, which is a division of application No. 17/026,051, filed on Sep. 18, 2020, now Pat. No. 11,253,534.

(60) Provisional application No. 63/022,371, filed on May 8, 2020, provisional application No. 63/022,368, filed on May 8, 2020, provisional application No. 63/002,494, filed on Mar. 31, 2020, provisional application No. 63/001,161, filed on Mar. 27, 2020, provisional application No. 62/993,345, filed on Mar. 23, 2020.

(51) Int. Cl.
| | | |
|---|---|---|
| *A61K 31/7052* | (2006.01) | |
| *A61K 31/375* | (2006.01) | |
| *A61K 33/30* | (2006.01) | |
| *A61P 31/14* | (2006.01) | |
| *A61K 31/593* | (2006.01) | |
| *A61K 31/4706* | (2006.01) | |

(52) U.S. Cl.
CPC ........ *A61K 31/7052* (2013.01); *A61K 31/375* (2013.01); *A61K 31/4706* (2013.01); *A61K 31/593* (2013.01); *A61K 33/30* (2013.01); *A61P 31/14* (2018.01)

(58) Field of Classification Search
CPC .. A61K 31/4706; A61K 31/375; A61K 31/59; A61K 31/592; A61K 31/593; A61K 31/315; A61K 33/30
See application file for complete search history.

(56) References Cited

U.S. PATENT DOCUMENTS

| | | |
|---|---|---|
| 7,026,360 B1 | 4/2006 | Festo |
| 7,351,739 B2 | 4/2008 | Ho et al. |
| 8,178,516 B2 | 5/2012 | Shapiro |
| 8,846,061 B1 | 9/2014 | Bezzek |
| 10,434,116 B2 | 10/2019 | Frieman et al. |
| 10,987,329 B1 | 4/2021 | Raju et al. |
| 11,166,971 B2* | 11/2021 | Hazan .................. A61K 33/30 |
| 11,253,534 B2* | 2/2022 | Hazan ................ A61K 31/7052 |
| 11,278,520 B2 | 3/2022 | Hazan |
| 2002/0155519 A1 | 10/2002 | Lindner et al. |
| 2004/0071757 A1 | 4/2004 | Rolf |
| 2005/0245502 A1* | 11/2005 | Keller .................... A61K 45/06 514/355 |
| 2006/0189542 A1 | 8/2006 | Furukawa et al. |
| 2006/0241059 A1* | 10/2006 | Keller ................ A61K 31/4704 514/276 |
| 2007/0026056 A1 | 2/2007 | Rolf |
| 2007/0031510 A1* | 2/2007 | Flavin-Koenig ..... A61K 36/484 514/440 |
| 2012/0077786 A1 | 3/2012 | Byron et al. |
| 2014/0147501 A1 | 5/2014 | Van Lengerich |
| 2014/0349969 A1 | 11/2014 | Penninger et al. |
| 2015/0309021 A1 | 10/2015 | Birnbaum et al. |
| 2016/0015786 A1 | 1/2016 | Levesque et al. |
| 2016/0095850 A1 | 4/2016 | Cooper et al. |
| 2017/0189443 A1 | 7/2017 | Parsons et al. |
| 2019/0085069 A1 | 3/2019 | Giles-Komar et al. |
| 2020/0085737 A1 | 3/2020 | Bellinger et al. |
| 2020/0102287 A1 | 4/2020 | Page et al. |
| 2020/0172480 A1 | 6/2020 | Zhao et al. |
| 2020/0237689 A1 | 7/2020 | Peralta et al. |
| 2021/0290697 A1 | 9/2021 | Hazan |
| 2021/0290718 A1 | 9/2021 | Hazan |
| 2021/0308167 A1 | 10/2021 | Hazan |
| 2022/0120746 A1 | 4/2022 | Hazan |
| 2022/0125819 A1 | 4/2022 | Hazan |

FOREIGN PATENT DOCUMENTS

| | | |
|---|---|---|
| CA | 1160570 | 1/1984 |
| EP | 1972341 A1 | 9/2008 |
| EP | 3513782 | 7/2019 |
| JP | 2014042514 | 3/2014 |

(Continued)

OTHER PUBLICATIONS

Gautret et al., "Hydroxychloroquine and azithromycin as a treatment of COVID-19: results of an open-label non-randomized clinical trial", Jul. 2020, published online Mar. 20, 2020, International Journal of Antimicrobial Agents, vol. 56, issue 1, pp. 1-6. (Year: 2020).*
Saul, "Vitamin C Protects Against Coronavirus", Jan. 26, 2020, Orthomolecular Medicine News Service, pp. 1-4. (Year: 2020).*
Malek et al., "Doxycycline as a potential partner of COVID-19 therapies", Jun. 6, 2020, IDCases, Elsevier Ltd., vol. 21, e00864, pp. 1-3. (Year: 2020).*
Youtube, Italian Covid-19 Patient in Rajasthan Tests Negative After Being Treated With HIV, Swine Flu and Malaria Drugs by Swarajya Staff. Mar. 13, 2020 at 7:10 PM. https://youtu.be/IR_W4s6LoYg News Brief.
Grimwood et al. "Vaccination against respiratory pseudomonas aeruginosa infection". Hum Vaccin Immunother. 2015;11(1):14-20. doi: 10.4161/hv.34296. Nov. 2014.

(Continued)

*Primary Examiner* — Michael B. Pallay
(74) *Attorney, Agent, or Firm* — Cislo & Thomas, LLP

(57) ABSTRACT

A method of treating an individual infected with COVID-19, the method comprising the steps of: providing an individual infected with COVID-19; and administering five antimicrobials to the individual, wherein the antimicrobials comprise: hydroxychloroquine; azithromycin; vitamin C; vitamin D; and zinc.

21 Claims, 6 Drawing Sheets

(56) References Cited

FOREIGN PATENT DOCUMENTS

| WO | WO0078268 | 12/2000 |
|----|-----------|---------|
| WO | WO2007023370 | 3/2007 |
| WO | WO2013040526 | 3/2013 |
| WO | WO2018161039 | 9/2018 |
| WO | WO2019051380 | 3/2019 |
| WO | WO2019199918 | 10/2019 |
| WO | WO2020051498 | 3/2020 |
| WO | WO2020214716 | 10/2020 |

OTHER PUBLICATIONS

"French researcher posts successful Covid-19 drug trial." The Connexion. Mar. 17, 2020. https://www.connexionfrance.com/French-news/French-researcher-in-Marseille-posts-successful-Covid-19-coronavirus-drug-trial-results.

Cao et al. "A Trial of Lopinavir-Ritonavir in Adults Hospitalized with Severe Covid-19." The New England Journal of Medicine. The New England Journal of Medicine, vol. 382, No. 19. May 2020. https://www.nejm.org/doi/full/10.1056/NEJMoa2001282?query=featured_home.

Banjanac et al. "Anti-Inflammatory Mechanism of Action of Azithromycin in LPS-Stimulated J774A.1 Cells." Pharmacological Research, vol. 66, No. 4, 2012, pp. 357-362., doi:10.1016/j.phrs.2012.06.011. Jul. 2012.

Cortegiani et al. "A Systematic Review on the Efficacy and Safety of Chloroquine for the Treatment of COVID-19." Journal of Critical Care, doi:10.1016/j.jcrc.2020.03.005. Mar. 2020.

Gao et al. "Breakthrough: Chloroquine Phosphate Has Shown Apparent Efficacy in Treatment of COVID-19 Associated Pneumonia in Clinical Studies." BioScience Trends, vol. 14, No. 1, pp. 72-73., doi:10.5582/bst.2020.01047. Feb. 2020.

Gautret et al. "Hydroxychloroquine and Azithromycin as a Treatment of COVID-19: Results of an Open-Label Non-Randomized Clinical Trial." International Journal of Antimicrobial Agents, p. 105949., doi:10.1016/j.jantimicag.2020.105949. Mar. 2020.

Gupta et al. "Clinical Considerations for Subjects with Diabetes in Times of COVID-19 Epidemic." Diabetes & Metabolic Syndrome: Clinical Research & Reviews, vol. 14, No. 3, pp. 211-212., doi:10.1016/j.dsx.2020.03.002. 2020.

Zhang et al. "Potential Interventions for Novel Coronavirus in China: A Systematic Review." Journal of Medical Virology, vol. 92, No. 5, pp. 479-490., doi: 10.1002/jmv.25707. Feb. 2020.

Saul, A. "Vitamin C Protects Against Coronavirus", Orthomolecular Medicine News Service, Jan. 26, 2020.

Lichtenstein, K. "Can Vitamin C Prevent and Treat Coronavirus?", medicinenet.com. Mar. 9, 2020.

Ferreira C, Viana SD, Reis F. Gut Microbiota Dysbiosis-Immune Hyperresponse-Inflammation Triad in Coronavirus Disease 2019 (COVID-19): Impact of Pharmacological and Nutraceutical Approaches. Microorganisms 2020; 8(10). Oct. 2020.

Yeoh YK, Zuo T, Lui GC, et al. Gut microbiota composition reflects disease severity and dysfunctional immune responses in patients with COVID-19. Gut 2021. Jan. 2021.

Zhou F, Yu T, Du R, et al. Clinical course and risk factors for mortality of adult inpatients with COVID-19 in Wuhan, China: a retrospective cohort study. Lancet 2020; 395(10229): 1054-62. Mar. 2020.

Gasbarrini G, Dionisi T, Franceschi F, Gasbarrini A. Editorial—COVID-19 and the microbiota: new kids on the block. Eur Rev Med Pharmacol Sci 2020; 24(9): 5189-91. Jan. 2020.

Janda L, Mihalcin M, Stastna M. Is a healthy microbiome responsible for lower mortality in COVID-19? Biologia (Bratisl) 2020: 1-11. Oct. 2020.

Galeotti C, Bayry J. Autoimmune and inflammatory diseases following COVID-19. Nat Rev Rheumatol 2020; 16(8): 413-4. Jun. 2020.

Tay MZ, Poh CM, Renia L, MacAry PA, Ng LFP. The trinity of COVID-19: immunity, inflammation and intervention. Nat Rev Immunol 2020; 20(6): 363-74. Apr. 2020.

Zuo T, Zhang F, Lui GCY, et al. Alterations in Gut Microbiota of Patients With COVID-19 During Time of Hospitalization. Gastroenterology 2020; 159(3): 944-55 e8. May 2020.

Ferreira C, Viana SD, Reis F. Is Gut Microbiota Dysbiosis a Predictor of Increased Susceptibility to Poor Outcome of COVID-19 Patients? An Update. Microorganisms 2020; 9(1). Dec. 2020.

Follmer C. Gut Microbiome Imbalance and Neuroinflammation: Impact of COVID-19 on Parkinson's Disease. Mov Disord 2020; 35(9): 1495-6. Aug. 2020.

Belancic A. Gut microbiome dysbiosis and endotoxemia—Additional pathophysiological explanation for increased COVID-19 severity in obesity. Obes Med 2020; 20: 100302. Sep. 2020.

Follmer C. Viral Infection-Induced Gut Dysbiosis, Neuroinflammation, and alpha-Synuclein Aggregation: Updates and Perspectives on COVID-19 and Neurodegenerative Disorders. ACS Chem Neurosci 2020; 11(24): 4012-6. Nov. 2020.

Zuo T, Zhan H, Zhang F, et al. Alterations in Fecal Fungal Microbiome of Patients With COVID-19 During Time of Hospitalization until Discharge. Gastroenterology 2020; 159(4): 1302-10 e5. Jun. 2020.

Kim HS. Do an Altered Gut Microbiota and an Associated Leaky Gut Affect COVID-19 Severity? mBio 2021; 12(1). Jan. 2021.

Gohil K, Samson R, Dastager S, Dharne M. Probiotics in the prophylaxis of COVID-19: something is better than nothing. 3 Biotech 2021; 11(1): 1. Nov. 2020.

Ahlawat S, Asha, Sharma KK. Immunological co-ordination between gut and lungs in SARS-CoV-2 infection. Virus Res 2020; 286: 198103. Jul. 2020.

Marsland BJ, Trompette A, Gollwitzer ES. The Gut-Lung Axis in Respiratory Disease. Ann Am Thorac Soc 2015; 12 Suppl 2: S150-6. May 2015.

Antunes AEC, Vinderola G, Xavier-Santos D, Sivieri K. Potential contribution of beneficial microbes to face the COVID-19 pandemic. Food Res Int 2020; 136: 109577. Jul. 17, 2020.

Alkhater SA. Dynamic Interplay Between Microbiota and Mucosal Immunity in Early Shaping of Asthma and its Implication for the COVID-19 Pandemic. J Asthma Allergy 2020; 13: 369-83. Sep. 2020.

Penninger JM, Grant MB, Sung JJY. The Role of Angiotensin Converting Enzyme 2 in Modulating Gut Microbiota, Intestinal Inflammation, and Coronavirus Infection. Gastroenterology 2021; 160(1): 39-46. Oct. 2020.

Assante G, Williams R, Youngson NA. Is the increased risk for MAFLD patients to develop severe COVID-19 linked to perturbation of the gut-liver axis? J Hepatol 2020. Jun. 2020.

Wang F, Zheng S, Zheng C, Sun X. Attaching clinical significance to COVID-19-associated diarrhea. Life Sci 2020; 260: 118312. Aug. 2020.

Meini S, Zini C, Passaleva MT, et al. Pneumatosis intestinalis in COVID-19. BMJ Open Gastroenterol 2020; 7(1). Jun. 2020.

Carding S, Verbeke K, Vipond DT, Corfe BM, Owen LJ. Dysbiosis of the gut microbiota in disease. Microb Ecol Health Dis 2015; 26: 26191. Feb. 2015.

Alam MT, Amos GCA, Murphy ARJ, Murch S, Wellington EMH, Arasaradnam RP. Microbial imbalance in Inflammatory bowel disease patients at different taxonomic levels. Gut Pathog 2020; 12: 1. Jan. 2020.

Hegde S, Lin YM, Golovko G, et al. Microbiota dysbiosis and its pathophysiological significance in bowel obstruction. Sci Rep 2018; 8(1): 13044. Sep. 2018.

Canoui E, Ingen-Housz-Oro S, Ortonne N, et al. [Hemophagocytic lymphohistiocytosis with granulomatosis and diffuse T-cell infiltration associated with disseminated Nocardiosis and pulmonary infection due to *Streptomyces* spp]. Rev Med Interne 2019; 40(7): 457-61. May 2019.

Bolourian A, Mojtahedi Z. *Streptomyces*, shared microbiome member of soil and gut, as 'old friends' against colon cancer. FEMS Microbiol Ecol 2018; 94(8). Jun. 2018.

Gureev AP, Shaforostova EA, Vitkalova IY, et al. Long-term mildronate treatment increased Proteobacteria level in gut microbiome, and caused behavioral deviations and transcriptome change in liver, heart and brain of healthy mice. Toxicol Appl Pharmacol 2020; 398: 115031. Jul. 2020.

(56) References Cited

OTHER PUBLICATIONS

Degruttola AK, Low D, Mizoguchi A, Mizoguchi E. Current Understanding of Dysbiosis in Disease in Human and Animal Models. Inflamm Bowel Dis 2016; 22(5): 1137-50. May 2016.

Bamola VD, Ghosh A, Kapardar RK, et al. Gut microbial diversity in health and disease: experience of healthy Indian subjects, and colon carcinoma and inflammatory bowel disease patients. Microb Ecol Health Dis 2017; 28(1): 1322447. Apr. 2017.

Nayfach S, Shi ZJ, Seshadri R, Pollard KS, Kyrpides NC. New insights from uncultivated genomes of the global human gut microbiome. Nature 2019; 568(7753): 505-10. Apr. 2019.

Rizzatti G, Lopetuso LR, Gibiino G, Binda C, Gasbarrini A. Proteobacteria: A Common Factor in Human Diseases. Biomed Res Int 2017; 2017: 9351507. Nov. 2017.

Rinninella E, Raoul P, Cintoni M, et al. What is the Healthy Gut Microbiota Composition? A Changing Ecosystem across Age, Environment, Diet, and Diseases. Microorganisms 2019; 7(1). Jan. 2019.

Shin NR, Whon TW, Bae JW. Proteobacteria: microbial signature of dysbiosis in gut microbiota. Trends Biotechnol 2015; 33(9): 496-503. Jul. 2015.

Pachikian BD, Neyrinck AM, Deldicque L, et al. Changes in intestinal bifidobacteria levels are associated with the Inflammatory response in magnesium-deficient mice. J Nutr 2010; 140(3): 509-14. Jan. 2010.

Suzuki A, Ito M, Hamaguchi T, et al. Quantification of hydrogen production by intestinal bacteria that are specifically dysregulated in Parkinson's disease. PLoS One 2018; 13(12): e0208313. Dec. 2018.

Cattaneo A, Cattane N, Galluzzi S, et al. Association of brain amyloidosis with proinflammatory gut bacterial taxa and peripheral inflammation markers in cognitively impaired elderly. Neurobiol Aging 2017; 49: 60-8. Aug. 2016.

Zaneveld Jr, McMinds R, Vega Thurber R. Stress and stability: applying the Anna Karenina principle to animal microbiomes. Nat Microbiol 2017; 2: 17121. Aug. 2017.

Mortensen EM, Coley CM, Singer DE, et al. Causes of death for patients with community-acquired pneumonia: results from the Pneumonia Patient Outcomes Research Team cohort study. Arch Intern Med 2002; 162(9): 1059-64. May 2002.

Alanio A, Delliere S, Fodil S, Bretagne S, Megarbane B. Prevalence of putative invasive pulmonary aspergillosis in critically ill patients with COVID-19. Lancet Respir Med 2020; 8(6): e48-e9. May 2020.

Steenwyk JL, Mead ME, de Castro PA, et al. Genomic and phenotypic analysis of COVID-19-associated pulmonary aspergillosis isolates of Aspergillus fumigatus. bioRxiv 2020. Nov. 2020.

Bruno G, Fabrizio C, Buccoliero GB. COVID-19-associated pulmonary aspergillosis: adding Insult to injury. Lancet Microbe 2020; 1(3): e106. Jul. 2020.

Lescure FX, Bouadma L, Nguyen D, et al. Clinical and virological data of the first cases of COVID-19 in Europe: a case series. Lancet Infect Dis 2020; 20(6): 697-706. Mar. 2020.

Kearns et al. "Large, single-dose, oral vitamin D supplementation in adult populations: a systematic review", Endocr Pract. Apr. 2014; 20 (4); 341-351.

PCT/US2021/023486, International Search Report and Written Opinion dated Jun. 8, 2021. 12 pages.

Lin, Dan-Yu et al; Effectiveness of Covid-19 Vaccines over a 9-Month Period in North Carolina, The New England Journal of Medicine, 386;10, publication date: Mar. 10, 2022 (Year: 2022); 9 pages.

Ware, Megan; "What is the nutritional value of mushrooms?", Medical News Today, publication date: Nov. 6, 2019 (Year: 2019); retrieved 2022; 12 pages.

The White House, National COVID-19 Preparedness Plan, www.whitehouse.gov/eovidplan, downloaded in May 2022 (Year: 2022); 11 pages.

Cooperman, Tod; Do any supplements help with the coronavirus (COVID-19)? Do supplements like vitamin D, zinc, vitamin C, or herbals work?, Consumer Lab, publication date: Mar. 6, 2020 (Year: 2020); retrieved 2022; 18 pages.

WHO, World Health Organization; Coronavirus disease (COVID-19) advice for the public: Mythbusters, publication date: Jan. 19, 2022 (Year: 2022); 17 pages.

Roxana Valdes Ramos (Effect of Vitamin C, D and Zinc Supplements on the Immune and Inflammatory Process in Type 2 Diabetic Subjects, ClinicalTrials.gov, US National Library of Medicine, First Posted: Nov. 8, 2018, Last Update Posted: Oct. 1, 2019 (Year: 2018); retrieved Jun. 28, 2023 (9 pages).

* cited by examiner

METHODS OF PREVENTING AND TREATING COVID-19 INFECTION

CROSS REFERENCE TO RELATED APPLICATIONS

This application is a continuation application of U.S. patent application Ser. No. 17/126,715, titled "Method of Preventing and Treating COVID-19 Infection," filed Dec. 18, 2020, which is a divisional application of U.S. patent application Ser. No. 17/026,051, titled "Method of Preventing and Treating COVID-19 Infection, filed Sep. 18, 2020, which claims priority to U.S. Provisional Patent Application No. 62/993,345, titled "Method of Treating and Preventing COVID-19 Infection," filed Mar. 23, 2020, U.S. Provisional Patent Application No. 63/022,371, titled "Method of Treating and Preventing COVID-19 Infection," filed May 8, 2020, U.S. Provisional Patent Application No. 63/002,494, titled "Method of Using Vitamin C, Vitamin D, Zinc, and Optionally Hydroxychloroquine, to Prevent COVID-19 Infection," filed Mar. 31, 2020, U.S. Provisional Patent Application No. 63/022,368, titled "Method of Using Vitamin C, Vitamin D, Zinc, and Optionally Hydroxychloroquine, to Prevent COVID-19 Infection," filed May 8, 2020, and U.S. Provisional Patent Application No. 63/001,161, titled "Method of Using Aerosolized Hydroxychloroquine, Vitamin C, and Zinc to Treat Covid-19 Infection," filed Mar. 27, 2020, the contents of which are incorporated by reference in their entirety.

BACKGROUND

COVID-19 is a novel betacoronavirus that originated in bats in the city of Wuhan, China. This disease has rapidly spread to become a worldwide pandemic, as declared by the World Health Organization (WHO). Symptoms of COVID-19, including fever, myalgia, coughing and shortness of breath, may appear from 2 and 14 days after exposure. Approximately 20% of patients progress to severe illness, including pneumonia, respiratory distress, and even death. Cases in the US have increased five-fold over the last week, alone. The disease is spreading rapidly, and a cure is desperately needed.

Nucleotide analogues, protease inhibitors and altered cellular bonding due to pH change will maximize host protection by: optimizing levels of gamma interferon and reducing the level of pathogenic microbes in the airways, especially in 'at risk' patients.

It is known that single anti-viral agents work poorly when used alone in other chronic viral infections such as Hepatitis C or HIV infection. Therefore, the greater the number of anti-viral agents used in combination, the greater the cure rate.

Thus, there is a significant unmet need for preventing and treating this viral infection. The present invention addresses this need.

SUMMARY

The invention herein is directed to my method of treating an individual infected with COVID-19. The method of treatment comprises the steps of: providing an individual infected with COVID-19 and administering five antimicrobials to the individual, wherein the antimicrobials comprise: chloroquine or hydroxychloroquine; azithromycin; vitamin C; vitamin D; and zinc.

Optionally, the method further comprises monitoring the individuals condition over a pre-determined period of time to determine whether the individual is no longer infected with COVID-19

Optionally, the method of treatment comprises administering hydroxychloroquine in daily dosage range of 20 mg to 2,000 mg; administering azithromycin in a daily dosage range of 250 mg to 500 mg; administering vitamin C in a daily dosage range of 250 mg to 10,000 mg, administering vitamin D in a daily dosage range of 1,000 mg to 100,000 mg; and administering zinc in a daily dosage range of 5 mg to 100 mg.

Optionally, the method of treatment comprises the steps of: administering, on day 1: two doses of 200 mg of hydroxychloroquine; one dose of 500 mg of azithromycin; one dose of 3,000 mg of vitamin C; one dose of 3,000 mg of vitamin D; and one dose of 50 mg of zinc; administering daily, on days 2 to 5: two doses of 200 mg of hydroxychloroquine; one dose of 250 mg of azithromycin; one dose of 3,000 mg of vitamin C; one dose of 3,000 mg of vitamin D; and one dose of 50 mg of zinc; and administering daily, on days 6 to 10: two doses of 200 mg of hydroxychloroquine; one dose of 3,000 mg of vitamin C; one dose of 3,000 mg of vitamin D; and one dose of 50 mg of zinc.

The antimicrobials can be administered orally in the form of an aerosolized spray.

The two doses of hydroxychloroquine can be administered as a single daily dose.

The method of treatment can further comprise administering daily, on days 6 to 10, administering one dose of 250 mg of azithromycin.

BRIEF DESCRIPTION OF THE DRAWINGS

Further advantages of the present invention may become apparent to those skilled in the art with the benefit of the following detailed description of the preferred embodiments and upon reference to the accompanying drawings in which.

DETAILED DESCRIPTION

Figure 1:
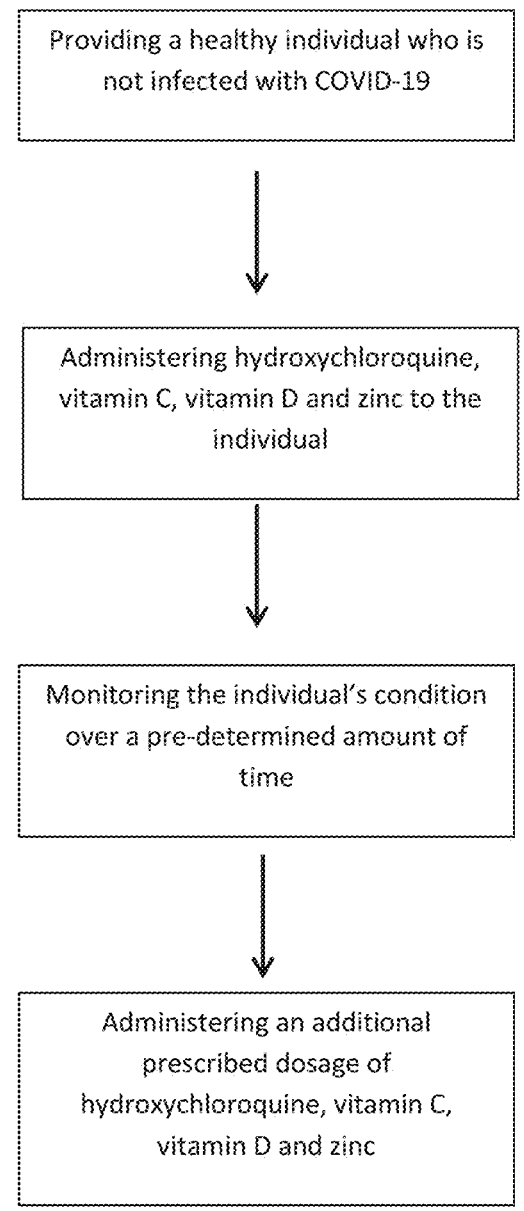
FIG. 1 is a flow chart depicting the steps of a method of preventing infection of an individual with COVID-19.

As used herein, the following terms and variations thereof have the meanings given below, unless a different meaning is clearly intended by the context in which such term is used.

The terms "a," "an," and "the" and similar referents used herein are to be construed to cover both the singular and the plural unless their usage in context indicates otherwise.

As used in this disclosure, the term "comprise" and variations of the term, such as "comprising" and "comprises," are not intended to exclude other additives, components, integers ingredients or steps.

Referring now to the drawings, wherein like reference numerals designate identical or corresponding features throughout the several views. Further, described herein are certain non-limiting embodiments of my pipeline filter assembly for pool filtering and maintenance.

The following discussion describes in detail multiple embodiments of the invention with several variations of those embodiments. This discussion should not be construed, however, as limiting the invention to those particular embodiments. Practitioners skilled in the art will recognize numerous other embodiments as well.

In a first embodiment, the present invention is directed to a method of preventing COVID-19 infection in an individual. The method involves administration of chloroquine or hydroxychloroquine, Vitamin C, Vitamin D, and Zinc. Both methods are discussed in greater detail below.

Referring now to FIG. 1, there is shown the method of prevention. The method of prevention comprises administering four different antimicrobials. The four antimicrobials comprise: chloroquine or hydroxychloroquine, vitamin C, vitamin D, and zinc.

Day 1 the individual takes the following, ideal, regimen outlined in Table 1:

TABLE 1

| Drug | AM Dose | PM Dose |
| --- | --- | --- |
| Hydroxychloroquine | 200 mg | 200 mg |
| Vitamin C | 3000 mg | — |
| Vitamin D | 3000 mg | — |
| Zinc | 50 mg | — |

Optionally, the method of prevention can comprise administering on day 2: 3,000 mg of vitamin C; 3,000 mg of vitamin D; and 50 mg of zinc.

Hydroxychloroquine is administered only on day 1. The half-life of hydroxychloroquine is up to 32 days, thus treatment with this drug for one day should be sufficient. However, should the need to prevent the infection or disease last longer than 32 days, repeat dosing can be considered. Accordingly, if necessary, the cycle of day 1 followed by day 2 can be repeated weekly, $2^{nd}$-weekly, every 3 weeks, 4 weeks, 5 weeks, 6 weeks, 7 weeks, or 8 weeks.

Vitamin C is administered at 3,000 mg per day ongoing. This 3,000 mg can be broken up into two 1500 mg doses, one taken in the morning and one taken at night.

Vitamin D is administered at 3,000 mg per day ongoing. This 3,000 mg can be broken up into two 1500 mg doses, one taken in the morning and one taken at night.

Zinc is administered at 50 mg per day ongoing. This 50 mg can be broken up into two 25 mg doses, one taken in the morning and one taken at night.

Chloroquine or hydroxychloroquine can be administered in a daily dosage range of 20 mg to 2,000 mg. The above amounts recited in the tables are not limiting.

Vitamin C can be administered in a daily dosage range of 250 mg to 10,000 mg. The above amounts recited in the tables are not limiting.

Vitamin D can be administered in a daily dosage rage of 1,000 mg to 100,000 mg. The above amounts recited in the tables are not limiting.

Zinc can be administered in a daily dosage of 5 mg to 100 mg. The amount of Zinc can be reduced to 25 mg per day if gastrointestinal upset occurs.

Zinc, Vitamin C and D help in numerous aspects of viral protection through cellular metabolism, including catalytic activity of enzymes, and play roles in immune function, protein synthesis.

The chloroquine or hydroxychloroquine can come in various forms: as a pill, liquid solution, lozenges, topical treatment such as a cream or oil, or any other means of delivery. Hydroxychloroquine prevents cytokine release, and cytokine release is what causes anaphylactic flush. Optionally, the hydroxychloroquine is sprayed directly on the users tongue.

In the method of prevention described above, all, or any combination of, the four antimicrobials disclosed above can be administered in the form of a single small atomizer. The patient sprays the atomizer towards the back of their throat. The spray is administered at least once a day, but preferably twice a day when coughing starts. Use of the atomizer continues as directed by the supervising physician.

Figure 2:
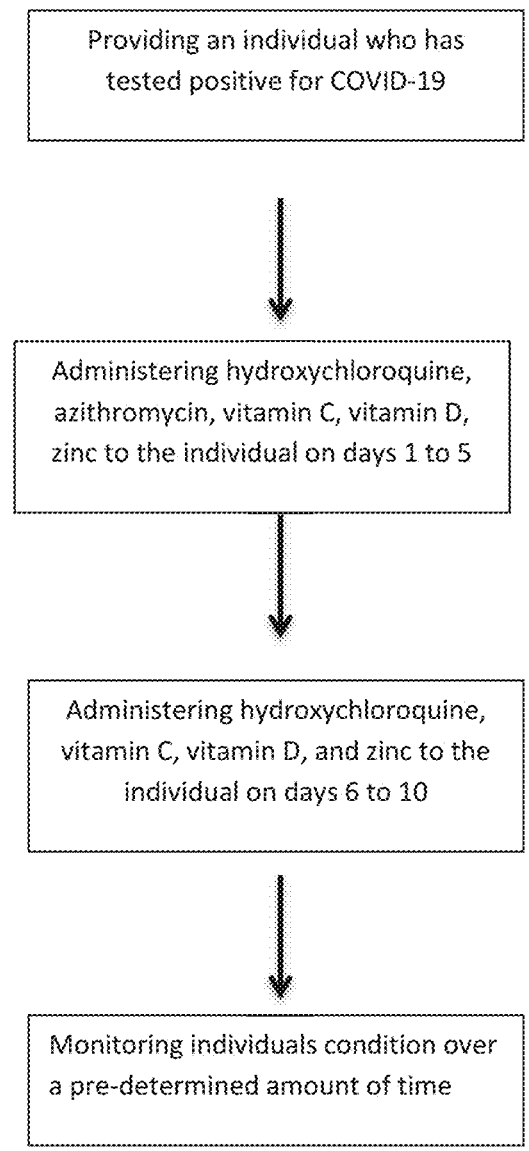
FIG. 2 is a flow chart depicting the steps of a method of treating an individual infected with COVID-19.
Figure 3A:
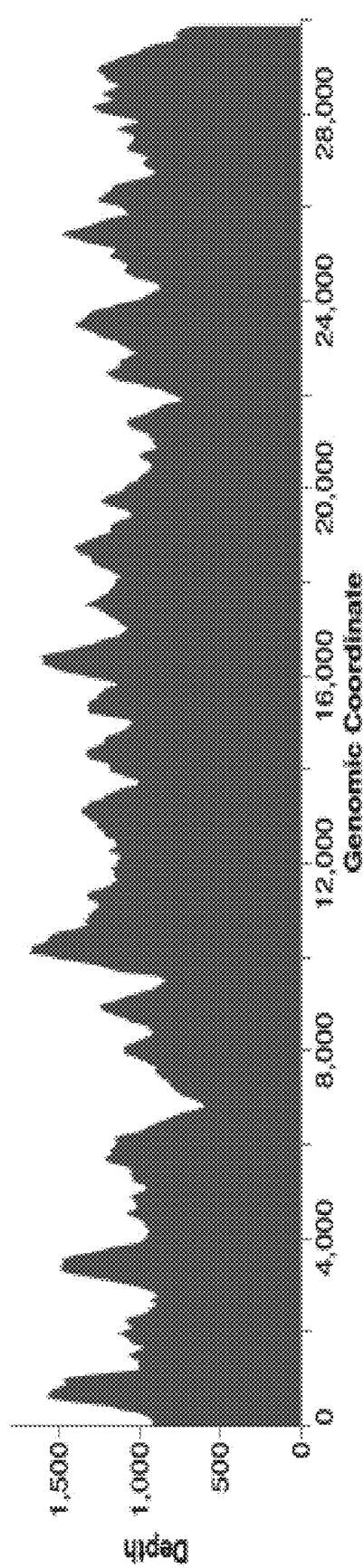
FIG. 3A a graphical representation of whole genome alignment of SARS-CoV-2 in patient 1 of Example 6.
Figure 3B:
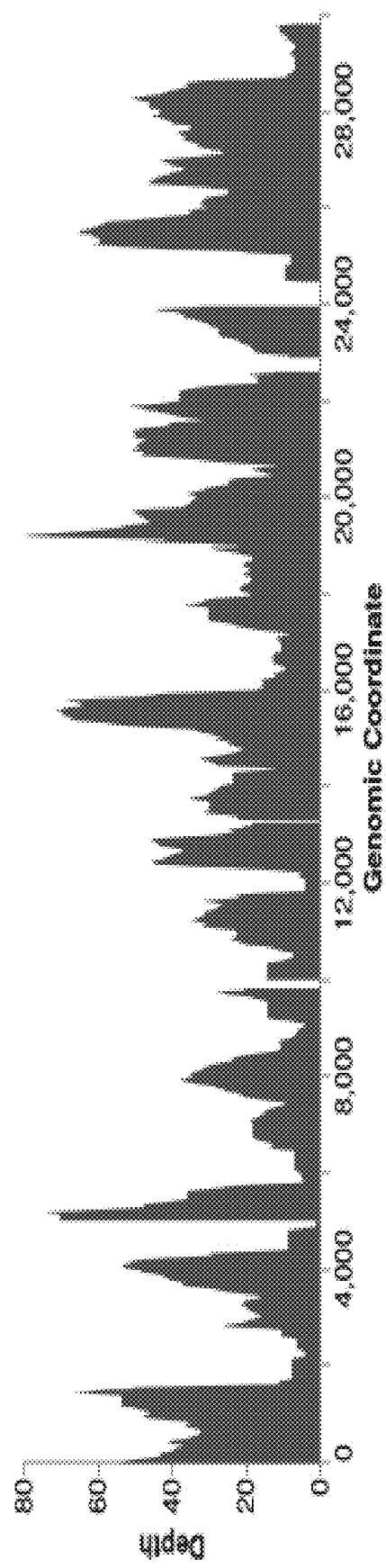
FIG. 3B a graphical representation of whole genome alignment of SARS-CoV-2 in patient 3 of Example 6.
Figure 3C:
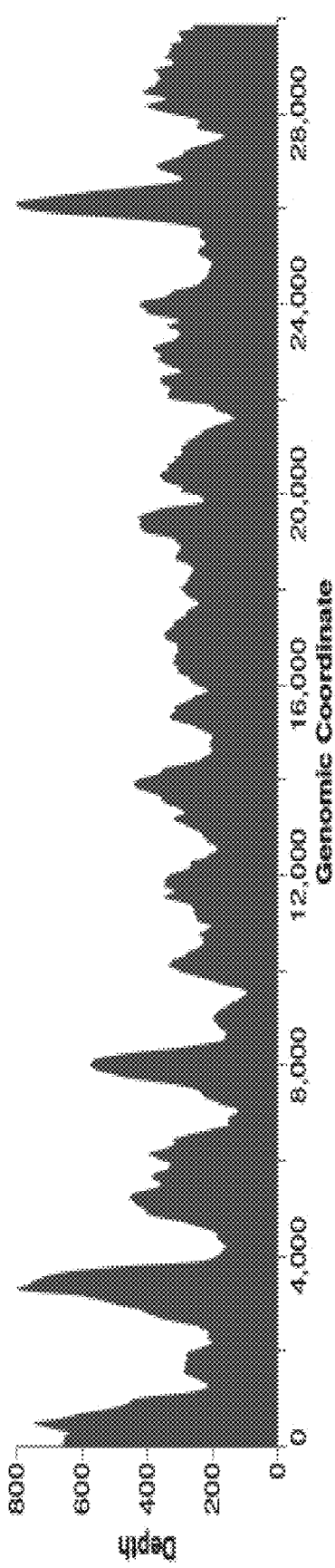
FIG. 3C a graphical representation of whole genome alignment of SARS-CoV-2 in patient 4 of Example 6.
Figure 3D:
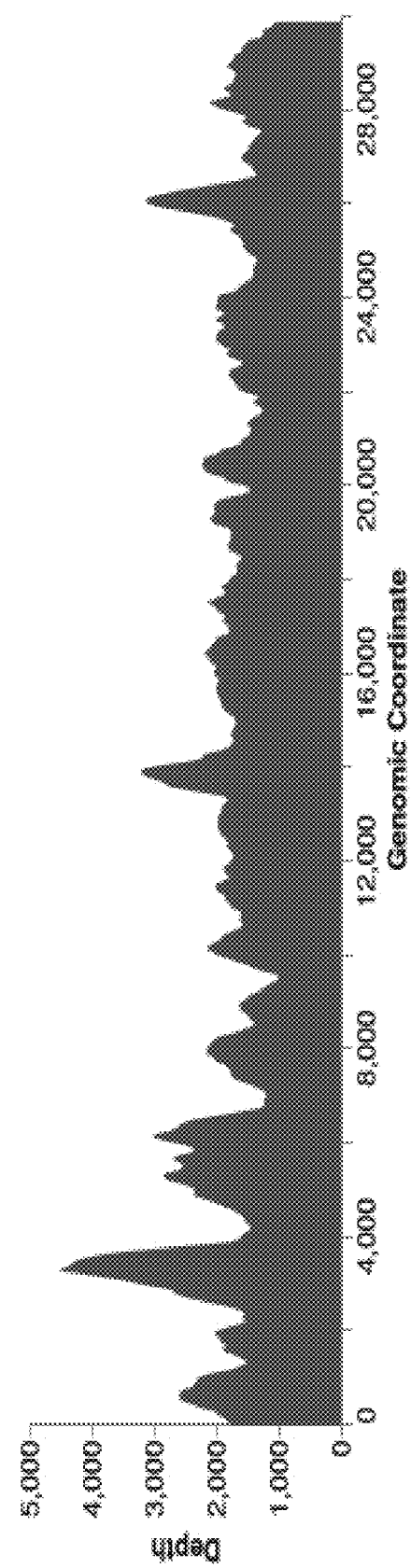
FIG. 3D a graphical representation of whole genome alignment of SARS-CoV-2 in patient 6 of Example 6.
Figure 3E:
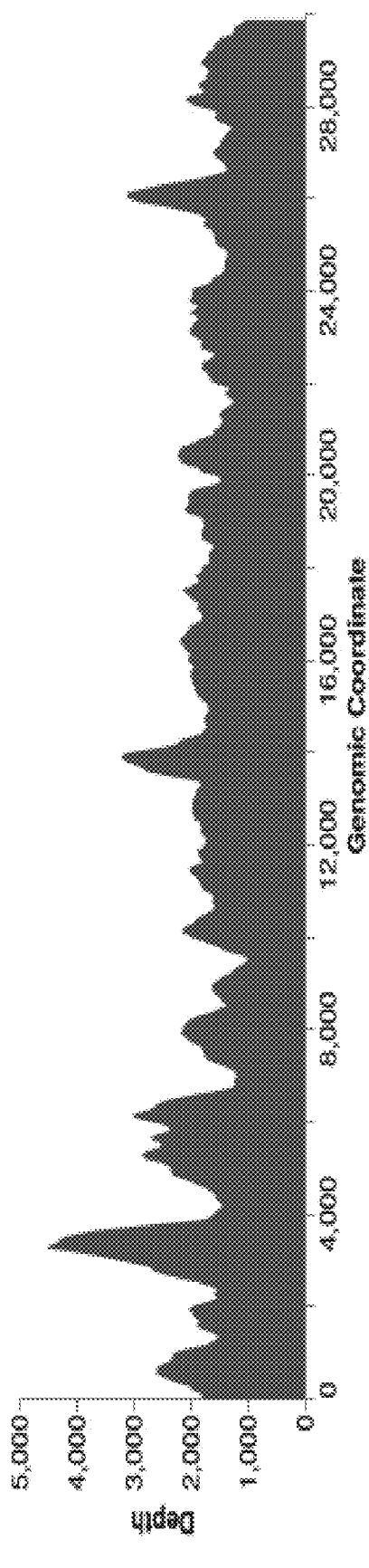
FIG. 3E a graphical representation of whole genome alignment of SARS-CoV-2 in patient 8 of Example 6.
Figure 3F:
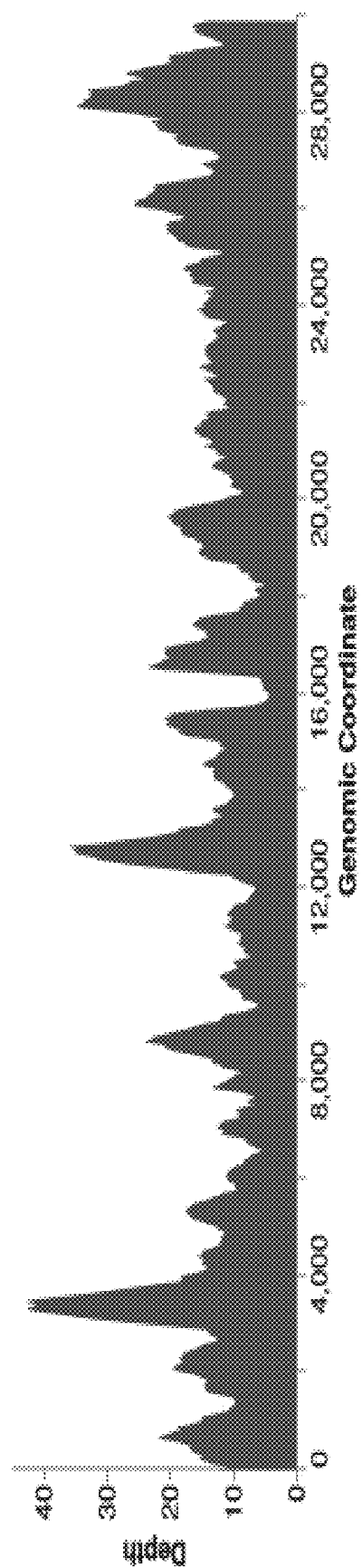
FIG. 3F a graphical representation of whole genome alignment of SARS-CoV-2 in patient 10 of Example 6.
Figure 3G:
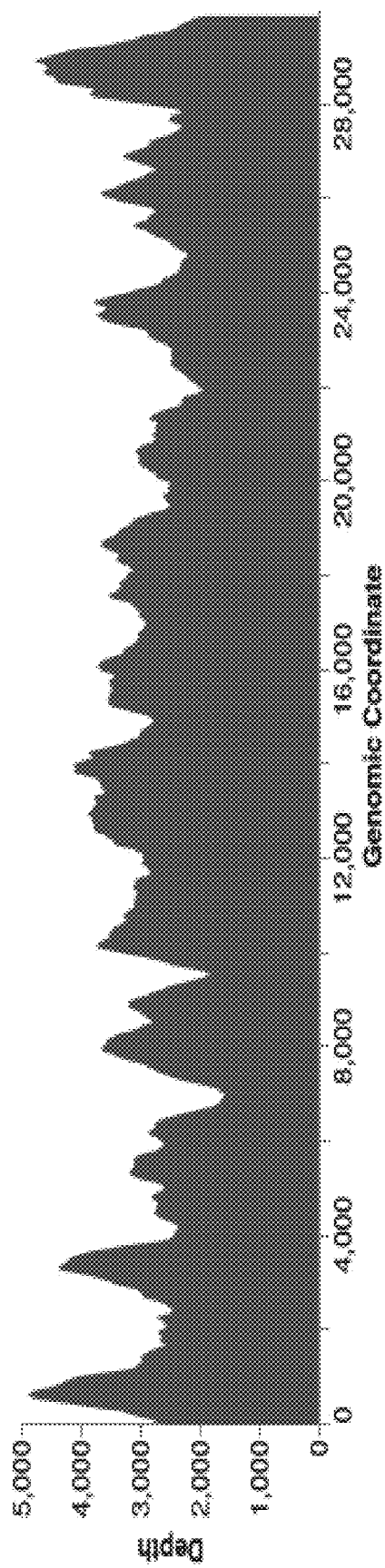
FIG. 3G a graphical representation of whole genome alignment of SARS-CoV-2 in patient 11 of Example 6.
Figure 3H:
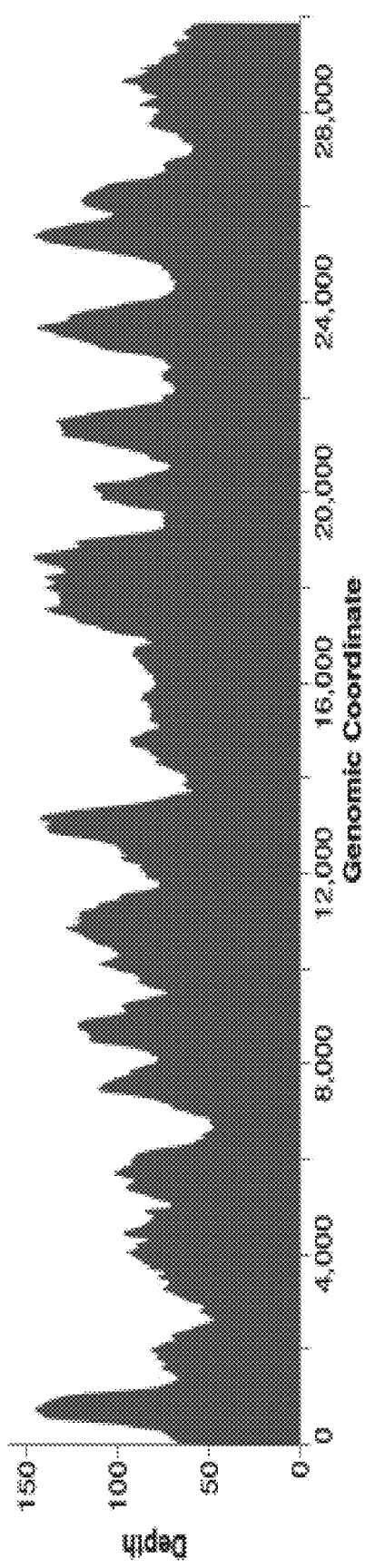
FIG. 3H a graphical representation of whole genome alignment of SARS-CoV-2 in patient 12 of Example 6.

In a second embodiment, the present invention is directed to a method of treating an individual with infection or disease with five different antimicrobials. The five antimicrobials comprise: hydroxychloroquine, azithromycin, vitamin C, vitamin D and zinc. Referring now to FIG. 2, there is shown the method of treatment.

Day 1 following positive test (isolation), the individual takes the following regimen outlined in Table 2:

TABLE 2

| Drug | AM Dose | PM Dose |
| --- | --- | --- |
| Hydroxychloroquine | 200 mg | 200 mg |
| Azithromycin | 500 mg | — |
| Vitamin C | 3000 mg | — |
| Vitamin D | 3000 mg | — |
| Zinc | 50 mg | — |

On Day 2-Day 5 the individual takes the following regimen outlined in Table 3:

TABLE 3

| Drug | AM Dose | PM Dose |
| --- | --- | --- |
| Hydroxychloroquine | 200 mg | 200 mg |
| Azithromycin | 250 mg | — |
| Vitamin C | 3000 mg | — |
| Vitamin D | 3000 mg | — |
| Zinc | 50 mg | — |

On Day 6-Day 10, the individual takes the following regimen outlined in Table 4:

TABLE 4

| Drug | AM Dose | PM Dose |
| --- | --- | --- |
| Hydroxychloroquine | 200 mg | 200 mg |
| Vitamin C | 3000 mg | — |
| Vitamin D | 3000 mg | — |
| Zinc | 50 mg | — |

Hydroxychloroquine is administered daily, at 200 mg twice daily for days 1-10.

Azithromycin is administered daily, at 500 mg on day 1, and 250 mg days 2-5. Optionally, azithromycin can be administered at 250 mg per day for 5-10 days with a loading dose of 500 mg x day 1 or simply 250 mg on day 1. Azithromycin may be substituted with doxycycline at a daily dosage range of 25 mg to 800 mg, for those unable to take azithromycin.

Vitamin C is administered at 3,000 mg per day ongoing. This 3,000 mg can be broken up into two 1500 mg doses, one taken in the morning and one taken at night.

Vitamin D is administered at 3,000 mg per day ongoing. This 3,000 mg can be broken up into two 1500 mg doses, one taken in the morning and one taken at night.

Zinc is administered at 50 mg per day ongoing. This 50 mg can be broken up into two 25 mg doses, one taken in the morning and one taken at night.

Chloroquine or hydroxychloroquine can be administered in a daily dosage range of 20 mg to 2,000 mg. The above amounts recited in the tables are not limiting.

Vitamin C can be administered in a daily dosage range of 250 mg to 10,000 mg. The above amounts recited in the tables are not limiting.

Vitamin D can be administered in a daily dosage rage of 1,000 mg to 100,000 mg. The above amounts recited in the tables are not limiting.

Zinc can be administered in a daily dosage of 5 mg to 100 mg. The amount of Zinc can be reduced to 25 mg per day if gastrointestinal upset occurs.

Concurrently with the above treatment, the individual is self-quarantined per CDC recommendations.

Optionally, for the method of treatment noted above, as the dosages of the hydroxychloroquine, vitamin C, vitamin D and zinc remain the same throughout treatment, all four of those antimicrobials can be administered in the form of a single small atomizer. The patient sprays the atomizer towards the back of their throat. The spray is administered at least once a day, but preferably twice a day when coughing starts. Use of the atomizer continues as directed by the supervising physician.

For all protocols provided in this application, vitamin C dosage can range from 250 mg to 10,000 mg per day, vitamin D dosage can range from 1000 IU (mg) to 100,000 IU (mg) per day, zinc (which can be any form or type of zinc) dosage can range from 5 mg to 100 mg per day, and hydroxychloroquine dosage can range from 50 mg to 2,000 mg per day for a treatment period of 1 to 10 days treatment. Optionally, hydroxychloroquine can be administered once as single dose. For all protocols provided in this application, when a dosage range is provided, any dosage amount that is included in that range can be administered. Accordingly, the invention is not limited to the dosage ranges disclosed, and includes all dosage amounts contained in those ranges.

Optionally, the above protocols can include selenium, copper and other vitamins that are deemed acceptable supplements for vitamin C, vitamin D or zinc or to counteract the negative depletion of certain vitamins, which is why copper or selenium are typically used.

Treatment can be for one day or consecutive or repeated in 2 weeks, 1 month, 6 months or 1 year, or weekly for 6 months.

The above protocols can be used to treat other viruses (not just COVID-19), including other flu and various respiratory viruses, including more benign coronaviruses and rhinoviruses.

The above protocols can also be used to treat Autism, Parkinson's, Alzheimer's and other neurological diseases.

EXAMPLES

Example 1: Hydroxychloroquine, Vitamin C, Vitamin D, and Zinc for Prevention of COVID-19 Infection Objective: To determine whether treatment with hydroxychloroquine, vitamin C, vitamin D, and zinc in combination will prevent infection with COVID-19 and to assess the safety and tolerability of hydroxychloroquine, vitamin C, vitamin D, and zinc in healthy, high-risk individuals without hypertension, and no evidence of COVID-19 infection.

Procedure: Day 1: Prescription of study drugs and home health monitoring equipment. The study drugs are hydroxychloroquine 200 mg twice a day for 1 day only, vitamin C 3000 mg per day ongoing, vitamin D 3000 mg per day ongoing, and zinc 50 mg per day ongoing per day. The home health monitoring equipment is an electrocardiogram (EKG) which synchs up with a smartphone Days 2-7: Patient collects the EKG once during this week using the home health equipment Weeks 1-23: Patient provides an assessment of any COVID-19 symptoms and continues to collect EKG weekly throughout the remainder of the trial Week 24: Patient undergoes confirmatory COVID-19 testing which consists of nasopharyngeal (NP) and oropharyngeal (OP) swabs collected according to CDC (Center for Disease Control) protocol. The swabs consist of synthetic fiber swabs with plastic shafts. NP swabs are collected by insertion of a swab into the nostril parallel to the palate. The swab is left in place a few seconds to allow it to absorb secretions. OP swabs are inserted into the oropharynx parallel to the palate, avoiding the tongue. The swab is left in place a few seconds to allow it to absorb secretions. The swabs are then immediately placed in sterile tubes with 2-3 mL of viral transport media. The tubes are placed in biohazard bags then boxes and couriered to the local Public Health Lab.

Table 5 provides a schedule of events for Example 1.

TABLE 5

| Assessment | Screening (Day 1) | Day 3 | Weeks 1-23 | Week 24 |
|---|---|---|---|---|
| Informed consent and demographics | X | | | |
| Review of prior and concomitant medications | X | | | |
| EKG at home | | X | X | |
| Prescription of Hydroxychloroquine, vitamin C, vitamin D, and zinc | X | | | |
| Provision of home health EKG and pulse oximeter | X | | | |
| Update list of prior and concomitant medications | X | | X | X |
| Ask about any adverse events and any serious adverse events | | X | X | X |
| Evaluation of COVID-19 symptoms | | | X | X |
| COVID-19 testing | | | | X |
| Blood draw for future testing | | | | X |
| Vitals in-clinic | | | | X |
| Physical exam | | | | X |

Regarding Table 5: Vitals at home to include EKG and O2Sat, future testing will require separate informed consent and could possibly include antibody or cytokine testing, and vitals in-clinic to include height, weight, blood pressure (following 5 minutes sitting) pulse, respiratory rate, temperature, and oxygen saturation.

Example 2: Randomized, Double-Blind, Placebo-Controlled Phase IIA Study of Hydroxychloroquine, Vitamin C, Vitamin D, and Zinc for the Prevention of COVID-19 Infection Objectives: Prevention of COVID-19, Lack of COVID-19 symptoms, and assessment of safety and tolerability Procedure: Screening Period (Days −5 to −1): Prescription of home health monitoring equipment that includes a thermometer, a pregnancy test if applicable, and a daily diary. There are two groups being studied: Arm 1 and Arm 2.

Arm 1 is prescribed the following antimicrobials: hydroxychloroquine 200 mg twice a day for 1 day only, vitamin C 3000 IU per day for 12 weeks, vitamin D 3000 IU per day for 12 weeks, and zinc 50 mg per day for 12 weeks. The zinc can be reduced to 25 mg if GI upset occurs.

Arm 2 is prescribed the following antimicrobials: Placebo twice a day for 1 day only, vitamin C 3000 IU per day for 12 weeks, vitamin D 3000 IU per day for 12 weeks, and zinc 50 mg per day for 12 weeks. The zinc can be reduced to 25 mg if GI upset occurs.

Day 1: Patient is called to teach them how to use the diary in the EDC, discuss the medication regimen, and answer any questions they may have. Patient takes pregnancy test if applicable, collects a temperature reading, completes their diary, and takes the prescribed treatment regimen. Table 6 outlines the prescribed treatment regimen for Day 1.

TABLE 6

| Drug | AM Dose | PM Dose |
| --- | --- | --- |
| Hydroxychloroquine (or placebo) | 200 mg | 200 mg |
| Vitamin C | 3000 mg | — |
| Vitamin D | 3000 IU | — |
| Zinc | 50 mg | — |

Day 2: Patient collects a temperature reading, completes their diary, and is called on the phone for assessment of any adverse events or serious adverse events, assessment of any COVID-19 symptoms, the list of prior and concomitant medications is updated, any questions the patient has are answered, and the patient takes their prescribed treatment regimen. Table 7 outlines the prescribed treatment regimen for Day 2.

TABLE 7

| Drug | AM Dose | PM Dose |
| --- | --- | --- |
| Vitamin C | 3000 mg | — |
| Vitamin D | 3000 IU | — |
| Zinc | 50 mg | — |

Days 3-10: Patient collects a temperature reading, completes their diary, and takes their prescribed treatment regimen. Table 8 outlines the prescribed treatment regimen for Days 3-10.

TABLE 8

| Drug | AM Dose | PM Dose |
| --- | --- | --- |
| Vitamin C | 3000 mg | — |
| Vitamin D | 3000 IU | — |
| Zinc | 50 mg | — |

Day 14: The patient is called for instruction on how to collect a nasal swab and package for shipping, assessment COVID-19 symptoms, updating their list of prior and concomitant medications, and answering any questions they may have.

Weeks 3-11: The patient is called weekly for assessment of any adverse events or serious adverse events, assessment of any COVID-19 symptoms, updating their list of prior and concomitant medications, and answering any questions they may have. The patient takes weekly temperature readings, completes their diary, and takes the prescribed treatment regimen. During Week 4 the patient is reminded to collect a nasal swab. The prescribed treatment regimen for Weeks 3-11 is shown in Table 9.

TABLE 9

| Drug | AM Dose | PM Dose |
| --- | --- | --- |
| Vitamin C | 3000 mg | — |
| Vitamin D | 3000 IU | — |
| Zinc | 50 mg | — |

Week 12: The patient presents to the clinic for evaluation that includes assessment for adverse events and serious adverse events, updating their list of prior and concomitant medications, a physical exam, nasal swab collection and COVID-19 sample collection.

Samples for COVID-19 testing are collected using synthetic swabs with plastic shafts. Nasal swabs are collected and immediately placed into a sterile vial with 2-3 mL of viral transport media. The vials are placed into biohazard bags, boxed up, the box sterilized, and picked up for shipment to the central laboratory. Samples are tested by RT-PCR.

Table 10 presents the schedule of events for Example 2.

TABLE 10

| Assessment | Screening | Day 1 | Day 2 | Day 3-10 | Day 14 | Weeks 3-12 | Month 1 | Month 2 | Month 3 |
| --- | --- | --- | --- | --- | --- | --- | --- | --- | --- |
| Informed Consent & Demographics | X | | | | | | | | |
| Initial Review of Prior and Concomitant Medications | X | | | | | | | | |
| Medical Records review, including baseline EKG | X | | | | | | | | |
| Randomization | X | | | | | | | | |
| Prescription of Hydroxychloroquine or placebo, vitamin C, vitamin D, and zinc | X | | | | | | | | |
| Provision of daily diary, thermometer and pregnancy test | X | | | | | | | | |

TABLE 10-continued

| Assessment | Screening | Day 1 | Day 2 | Day 3-10 | Day 14 | Weeks 3-12 | Month 1 | Month 2 | Month 3 |
|---|---|---|---|---|---|---|---|---|---|
| Pregnancy Test if applicable | | X | | | | | | | |
| Temperature at home | | X | X | X | X | X | X | X | X |
| Complete daily diary | | X | X | X | X | X | X | X | X |
| Hydroxychloroquine 200 mg | | X | | | | | | | |
| Vitamin C 3000 mg | | X | X | X | X | X | X | X | X |
| Vitamin D 3000 IU | | X | X | X | X | X | X | X | X |
| Zinc 50 mg[a] | | X | X | X | X | X | X | X | X |
| Phone/video call to patient[b] | X | X | X | | X | X | X | X | |
| Update list of prior and concomitant medications | | X | X | X | X | X | X | X | X |
| Ask about AE and SAE | | X | X | X | X | X | X | X | X |
| Assessment of COVID-19 symptoms | | X | X | X | X | X | X | X | X |
| Swabs for RT-PCR | | | | | X | | X | | X |
| Vitals in-clinic[c] | | | | | | | | | X |
| Physical Exam | | | | | | | | | X |

Regarding Table 10: The Zinc may be reduced to 25 mg if GI upset occurs, phone/video calls to the patient occur weekly during Weeks 2-11, and vitals in-clinic include height, weight, blood pressure (following 5 minutes sitting) pulse, respiratory rate, temperature, and oxygen saturation.

Statistical Analysis: The treated patients in this study are compared to the placebo group. Measurements include PCR test results, presence or absence of symptoms, and symptom severity.

The change of these measurements from the end to the baseline (post-pre) are used as the primary outcome, for example, $\mu e = \mu e1 - \mu e0$, where $\mu e1$ and $\mu e0$ are the outcome of patients from the treatment group at the end and at baseline, respectively.

$H_0$: $\Delta \leq \delta_0$ against $H_a$: $\Delta > \delta_0$ where $\delta_0$ is a clinically meaningful threshold to measure the disease symptoms. In this study, that meaningful threshold is calculated as mean change in clinical symptoms as recorded in the diary, from baseline through week 12. Each category in the diary is assigned a number, 0 for None, 1 for Mild, 2 for Moderate and 3 for severe. Each category is analyzed independently and as a group.

Categorical variables are summarized by presenting the number (n) and percent (%) of subjects in each category. All Statistical tests for the analysis are performed using the $p<0.05$ level of significance. All confidence intervals are one-sided.

Since these are healthcare workers who are exposed to COVID-19 at every shift, efficacy is determined by RT-PCR testing, as well as the presence or absence of symptoms as recorded in the patient diary via EDC.

Example 3: Use of Hydroxychloroquine, Azithromycin, Vitamin C, Vitamin D, and Zinc to Treat COVID-19 Infection Objectives: test the efficacy of hydroxychloroquine, azithromycin, vitamin C, vitamin D, and zinc in the treatment of patients with COVID-19 infection and to assess the safety and tolerability of this treatment in patients with COVID-19 infection.

Procedure: First, the patient is determined to have COVID-19.

Day 1 following positive test (isolation): The patient takes prescribed regimen outlined in Table 11.

TABLE 11

| Drug | AM Dose | PM Dose |
|---|---|---|
| Hydroxychloroquine | 200 mg | 200 mg |
| Azithromycin | 500 mg | — |
| Vitamin C | 3000 mg | — |
| Vitamin D | 3000 mg | — |
| Zinc | 50 mg | — |

Day 2-Day 5: The patient takes the prescribed regimen outlined in Table 12.

TABLE 12

| Drug | AM Dose | PM Dose |
|---|---|---|
| Hydroxychloroquine | 200 mg | 200 mg |
| Azithromycin | 250 mg | — |
| Vitamin C | 3000 mg | — |
| Vitamin D | 3000 mg | — |
| Zinc | 50 mg | — |

Day 6-Day 10: The patient takes the prescribed regimen outlined in Table 13.

TABLE 13

| Drug | AM Dose | PM Dose |
|---|---|---|
| Hydroxychloroquine | 200 mg | 200 mg |
| Vitamin C | 3000 mg | — |
| Vitamin D | 3000 mg | — |
| Zinc | 50 mg | — |

Follow-Up Period: Month 1 (outpatient only AFTER negative test): vital signs are taken that include blood pressure, heart rate, respiratory rate, oxygen saturation, temperature), the patient is assessed for adverse events and serious adverse events, and swabs for PCR are taken.

Month 3 (outpatient): vital signs are taken that include blood pressure, heart rate, respiratory rate, oxygen saturation, temperature), the patient is assessed for adverse events and serious adverse events, and swabs for PCR are taken.

Month 6 (outpatient) vital signs are taken that include blood pressure, heart rate, respiratory rate, oxygen saturation, temperature), the patient is assessed for adverse events and serious adverse events, and swabs for PCR are taken.

Month 9 (outpatient) vital signs are taken that include blood pressure, heart rate, respiratory rate, oxygen saturation, temperature), the patient is assessed for adverse events and serious adverse events, and swabs for PCR are taken.

Month 12 (outpatient) vital signs are taken that include blood pressure, heart rate, respiratory rate, oxygen saturation, temperature), the patient is assessed for adverse events and serious adverse events, and swabs for PCR are taken.

COVID-19 sample collection procedure is as follows: nasopharyngeal (NP) and oropharyngeal (OP) swabs are collected according to CDC protocol. The swabs comprise synthetic fiber swabs with plastic shafts. NP swabs are collected by insertion of a swab into the nostril parallel to the palate. The swab is left in place a few seconds to allow it to absorb secretions. OP swabs are inserted into the oropharynx parallel to the palate, avoiding the tongue. The swab is left in place a few seconds to allow it to absorb secretions. NP and OP swabs are immediately placed in sterile tubes with 2-3 mL of viral transport media. The tubes are placed in biohazard bags then boxes and couriered to the local Public Health Lab. Table 14 outlines the schedule of events for Example 3.

Arm 1 is prescribed the following antimicrobials: Hydroxychloroquine 200 MG BID for 10 days; Azithromycin 500 mg on day 1, 250 mg day 2-5; Vitamin C 3000 mg for 10 days, then 1500 mg for 20 days; Vitamin D 3000 IU for 10 days, then 1500 IU for 20 days; and Zinc 50 mg for 10 days, then 25 mg for 20 days.

Arm 2 is prescribed the following antimicrobials: Placebo for Hydroxychloroquine BID for 10 days. Placebo for Azithromycin to be taken 2 the on Day 1, then 1 on Days 2-5 Vitamin C 3000 mg for 10 days, then 1500 mg for 20 days; Vitamin D 3000 IU for 10 days, then 1500 IU for 20 days; and Zinc 50 mg for 10 days, then 25 mg for 20 days. Table 16 outlines the prescribed antimicrobials discussed above.

TABLE 14

| Assessment | Diagnosis and Rx (Day 1) | Day 1→7 | Month 1 (±4 d) | Month 3 (±4 d) | Month 6 (±4 d) | Month 9 (±4 d) | Month 12 (+4 d) |
|---|---|---|---|---|---|---|---|
| Informed Consent & Demographics | X | | | | | | |
| Confirmation of Positive PCR for COVID-19 | X | | | | | | |
| Review of Medical Records | X | | | | | | |
| Vitals[a] | | | X | X | X | X | X |
| Prescription of Antimicrobials[b] | X | | | | | | |
| Ask about AE and SAE | | X | X | X | X | X | X |

Regarding Table 14: Vitals to include height (only at first visit), weight, blood pressure (following 5 minutes sitting) pulse, respiratory rate, temperature, and oxygen saturation. Dosage to be given as in section 8, below Table 15 provides a summary of the antimicrobial dosage of Example 3.

TABLE 15

| Treatment Method | Medication | Dose | Frequency |
|---|---|---|---|
| Quintuple Therapy | Hydroxychloroquine | 200 mg | BID |
| | Azithromycin | 500 mg\Day 1 → 250 mg Day 2-5 | Daily |
| | Vitamin C | 3000 mg | Daily |
| | Vitamin D | 5000 mg | Daily |
| | Zinc | 50 mg | Daily |

Example 4: Randomized, Double-Blind, Placebo-Controlled Phase IIA Study of Hydroxychloroquine, Azithromycin, Vitamin C, Vitamin D, and Zinc to Treat COVID-19 Infection Objectives: Test the efficacy of hydroxychloroquine, azithromycin, vitamin C, vitamin D, and zinc in the treatment of patients with COVID-19 infection and to assess the safety and tolerability of this treatment in patients with COVID-19 infection.

Procedure: First, the patient's diagnosis of COVID-19 infection is confirmed.

Screening Period (Days −3 to −1): Prescription of home health monitoring equipment that includes a thermometer, a pulse oximeter, a pregnancy test if applicable, and a daily diary. There are two groups being studied: Arm 1 and Arm 2.

TABLE 16

| Treatment Method | Medication | Dose | Frequency |
|---|---|---|---|
| Quintuple Therapy | Hydroxychloroquine | 200 mg | BID |
| | Azithromycin | 500 mg\Day 1 → 250 mg Day 2-5 | Daily |
| | Vitamin C | 3000 mg | Daily |
| | Vitamin D | 5000 mg | Daily |
| | Zinc | 50 mg | Daily |
| Placebo | Placebo | 1 tablet | BID |
| | Placebo | 2 tablets day 1, then 1 tablet day 2-5 | Daily |
| | Vitamin C | 3000 mg | Daily |
| | Vitamin D | 3000 IU | Daily |
| | Zinc | 50 mg | Daily |

Treatment Period: Day 1 following positive test (isolation), the patient is video called to ensure they have all study materials and the following is discussed: Use of home health equipment, Subject will take baseline measurements at this time and record it in the diary, Diary and how to transmit its contents, Medication dosing, Subject will take pregnancy test if applicable, Subject will use provided equipment to measure vital signs such as EKG, Oxygen Saturation, and Temperature. The patient takes prescribed regimen outlined in Table 17.

TABLE 17

| Drug | AM Dose | PM Dose |
|---|---|---|
| Hydroxychloroquine (or Placebo) | 200 mg | 200 mg |
| Azithromycin (or Placebo) | 500 mg | — |
| Vitamin C | 3000 mg | — |

TABLE 17-continued

| Drug | AM Dose | PM Dose |
| --- | --- | --- |
| Vitamin D | 3000 IU | — |
| Zinc | 50 mg | — |

Day 2: The patient completes the AM and PM diary entries, the patient uses the provided equipment to measure vital signs such as EKG, Oxygen saturation, and temperature, and the patient takes the prescribed regimen outlined in Table 18.

TABLE 18

| Drug | AM Dose | PM Dose |
| --- | --- | --- |
| Hydroxychloroquine (or Placebo) | 200 mg | 200 mg |
| Azithromycin (or Placebo) | 250 mg | — |
| Vitamin C | 3000 mg | — |
| Vitamin D | 3000 IU | — |
| Zinc | 50 mg | — |

Day 3: The patient is called and asked if they are experiencing any difficulties with swab collection, whether there have been any adverse events and/or serious adverse events, the list of prior and concomitant medications is updated, the patient is asked about symptom resolution or progression, the patient is instructed on how to collect nasal swabs, and the patient then collects the first nasal swab. The patient completes their AM and PM diary entries, and collects their vital signs such as EKG, oxygen saturation and temperature. The patient takes the prescribed regimen outlined in Table 19.

TABLE 19

| Drug | AM Dose | PM Dose |
| --- | --- | --- |
| Hydroxychloroquine (or Placebo) | 200 mg | 200 mg |
| Azithromycin (or Placebo) | 250 mg | — |
| Vitamin C | 3000 mg | — |
| Vitamin D | 3000 IU | — |
| Zinc | 50 mg | — |

Day 4: The patient completes their AM and PM diary entries, collects their vital signs, and takes the prescribed regimen outlined in Table 20.

TABLE 20

| Drug | AM Dose | PM Dose |
| --- | --- | --- |
| Hydroxychloroquine (or Placebo) | 200 mg | 200 mg |
| Azithromycin (or Placebo) | 250 mg | — |
| Vitamin C | 3000 mg | — |
| Vitamin D | 3000 IU | — |
| Zinc | 50 mg | — |

Day 5: The patient completes their AM and PM diary entries, collects their vital signs, collects a nasal swab, and takes the prescribed regimen outlined in Table 21.

TABLE 21

| Drug | AM Dose | PM Dose |
| --- | --- | --- |
| Hydroxychloroquine (or Placebo) | 200 mg | 200 mg |
| Azithromycin (or Placebo) | 250 mg | — |
| Vitamin C | 3000 mg | — |
| Vitamin D | 3000 IU | — |
| Zinc | 50 mg | — |

Day 6: The patient completes their AM and PM diary entries, collects their vital signs, and takes the prescribed regimen outlined in Table 22.

TABLE 22

| Drug | AM Dose | PM Dose |
| --- | --- | --- |
| Hydroxychloroquine (or Placebo) | 200 mg | 200 mg |
| Vitamin C | 3000 mg | — |
| Vitamin D | 3000 IU | — |
| Zinc | 50 mg | — |

Day 7: The patient is called and asked whether there have been any adverse events and/or serious adverse events, the list of prior and concomitant medications is updated, the patient is asked about symptom resolution or progression, and the patient then collects a nasal swab. The patient also completes their AM and PM diary entries and collects their vital signs. The patient takes the prescribed regimen outlined in Table 23.

TABLE 23

| Drug | AM Dose | PM Dose |
| --- | --- | --- |
| Hydroxychloroquine (or Placebo) | 200 mg | 200 mg |
| Vitamin C | 3000 mg | — |
| Vitamin D | 3000 IU | — |
| Zinc | 50 mg | — |

Day 8: The patient completes their AM and PM diary entries, collects their vital signs, and takes the prescribed regimen outlined in Table 24.

TABLE 24

| Drug | AM Dose | PM Dose |
| --- | --- | --- |
| Hydroxychloroquine (or Placebo) | 200 mg | 200 mg |
| Vitamin C | 3000 mg | — |
| Vitamin D | 3000 IU | — |
| Zinc | 50 mg | — |

Day 9: The patient completes their AM and PM diary entries, collects their vital signs, and takes the prescribed regimen outlined in Table 25.

TABLE 25

| Drug | AM Dose | PM Dose |
| --- | --- | --- |
| Hydroxychloroquine (or Placebo) | 200 mg | 200 mg |
| Vitamin C | 3000 mg | — |
| Vitamin D | 3000 IU | — |
| Zinc | 50 mg | — |

Day 10: The patient is called reminded to decrease dosage of vitamins C, Vitamin D, and zinc tomorrow. The patient is asked whether there have been any adverse events and/or serious adverse events, the list of prior and concomitant medications is updated, and the patient is asked about symptom resolution or progression. The patient also completes their AM and PM diary entries and collects their vital signs. The patient takes the prescribed regimen outlined in Table 26.

TABLE 26

| Drug | AM Dose | PM Dose |
| --- | --- | --- |
| Hydroxychloroquine (or Placebo) | 200 mg | 200 mg |
| Vitamin C | 3000 mg | — |
| Vitamin D | 3000 IU | — |
| Zinc | 50 mg | — |

Day 11 to Day 13: The patient completes their AM and PM diary entries and takes the prescribed regimen outlined in Table 27.

TABLE 27

| Drug | AM Dose | PM Dose |
| --- | --- | --- |
| Vitamin C | 1500 mg | — |
| Vitamin D | 1500 IU | — |
| Zinc | 25 mg | — |

Day 14: The patient is called and asked whether there have been any adverse events and/or serious adverse events, the patient is asked about symptom resolution or progression, and the patient then collects a nasal swab. The patient also completes their AM and PM diary entries and collects their vital signs. The patient takes the prescribed regimen outlined in Table 28.

TABLE 28

| Drug | AM Dose | PM Dose |
| --- | --- | --- |
| Vitamin C | 1500 mg | — |
| Vitamin D | 1500 IU | — |
| Zinc | 25 mg | — |

Day 15 to Day 30: The patient completes their AM and PM diary entries and takes the prescribed regimen outlined in Table 29.

TABLE 29

| Drug | AM Dose | PM Dose |
| --- | --- | --- |
| Vitamin C | 1500 mg | — |
| Vitamin D | 1500 IU | — |
| Zinc | 25 mg | — |

Follow-Up Period: Month 1 (outpatient only AFTER negative test): Vital signs are taken (BP, HR, RR, oxygen saturation, temperature), the patient is assessed for adverse events and/or serious adverse events, and EKG is administered as well as physical exam and a blood draw for CBC/Complete metabolic panel/C-Reactive Protein. The list of prior and concomitant medications is updated and a nasal swab is collected.

Month 2 (outpatient): Vital signs are collected (BP, HR, RR, oxygen saturation, temperature) the patient is assessed for adverse events and/or serious adverse events, and EKG is administered as well as physical exam and a blood draw for CBC/Complete metabolic panel/C-Reactive Protein. The list of prior and concomitant medications is updated.

Month 3 (outpatient): Vital signs are taken (BP, HR, RR, oxygen saturation, temperature), the patient is assessed for adverse events and/or serious adverse events, and EKG is administered as well as physical exam and a blood draw for CBC/Complete metabolic panel/C-Reactive Protein. The list of prior and concomitant medications is updated and a nasal swab is collected.

COVID-19 Sample Collection Procedure is the same as that outlined above in prior Examples. Table 30 outlines the schedule of events for Example 4.

TABLE 30

| Assessment | Screening (Da-3 to Day-1) | Day 1 | Day 2 | Day 3 | Day 4 | Day 5 | Day 6 | Day 7 | Day 8 | Day 9 |
| --- | --- | --- | --- | --- | --- | --- | --- | --- | --- | --- |
| Informed Consent & Demographics | X | | | | | | | | | |
| Make list of prior and concomitant medications | X | | | X | | | | X | | |
| Confirmation of Positive PCR for COVID-19 | X | | | | | | | | | |
| Review of Medical Records | X | | | | | | | | | |
| Prescription of Antimicrobials[a] | X | | | | | | | | | |
| Provide home health equipment[b] | X | | | | | | | | | |
| Pregnancy test[c] | | X | | | | | | | | |
| Call Subject at home[d] | | X | X | | | | | X | | |
| Vitals at home[e] | | X | X | X | X | X | X | X | X | X |

TABLE 30-continued

| Assessment | | | | | | | | | |
|---|---|---|---|---|---|---|---|---|---|
| Subject will complete AM/PM diary | X | X | X | X | X | X | X | X | X |
| Hydroxychloroquine 200 mg BID (or placebo) | X | X | X | X | X | X | X | X | X |
| Azithromycin 500 mg (2 tablets) once daily (or placebo) | X | | | | | | | | |
| Azithromycin 250 mg (1 tablet) once daity (or placebo) | | X | X | X | X | | | | |
| Vitamin C 3000 mg (4 capsules) once daily | | X | X | X | X | X | X | X | X |
| Vitamin D 3000 IU (4 capsules) once daily | | X | X | X | X | X | X | X | X |
| Zinc 50 mg (4 capsules) once daily | | X | X | X | X | X | X | X | X |
| Vitamin C 1500 mg (2 capsides) once daily | | | | | | | | | |
| Vitamin D 1500 IU (2 capsules) once daily | | | | | | | | | |
| Zinc 25 mg (2 capsules) once daily | | | | | | | | | |
| Ask about AE and SAE | | | X | | | | X | | |
| Vitals in-clinic[f] | | | | | | | | | |
| Physical exam | | | | | | | | | |
| EKG in-clinic | | | | | | | | | |
| Swabs for RT-PCR | | | X | | X | | X | | |
| Bloodwork[g] | | | | | | | | | |
| Review list of prior and concomitant medications | X | X | X | X | X | X | X | X | X |

| Assessment | Day 10 | Day 11 | Day 12 | Day 13 | Day 14 | Days 15-30 | Month 1 | Month 2 | Month 3 |
|---|---|---|---|---|---|---|---|---|---|
| Informed Consent & Demographics | | | | | | | | | |
| Make list of prior and concomitant medications | X | | | | X | | X | X | X |
| Confirmation of Positive PCR for COVID-19 | | | | | | | | | |
| Review of Medical Records | | | | | | | | | |
| Prescription of Antimicrobials[a] | | | | | | | | | |
| Provide home health equipment[b] | | | | | | | | | |
| Pregnancy test[c] | | | | | | | | | |
| Call Subject at home[d] | X | | | | X | | | | |
| Vitals at home[e] | X | | | | | | | | |
| Subject will complete AM/PM diary | X | X | X | X | X | X | | | |

TABLE 30-continued

| | 1 | 2 | 3 | 4 | 5 | 6 | 7 | 8 | 9 |
|---|---|---|---|---|---|---|---|---|---|
| Hydroxychloroquine 200 mg BID (or placebo | X | | | | | | | | |
| Azithromycin 500 mg (2 tablets) once daily (or placebo) | | | | | | | | | |
| Azithromycin 250 mg (1 tablet) once daity (or placebo) | | | | | | | | | |
| Vitamin C 3000 mg (4 capsules) once daily | X | | | | | | | | |
| Vitamin D 3000 IU (4 capsules) once daily | X | | | | | | | | |
| Zinc 50 mg (4 capsules) once daily | X | | | | | | | | |
| Vitamin C 1500 mg (2 capsides) once daily | | X | X | X | X | X | | | |
| Vitamin D 1500 IU (2 capsules) once daily | | X | X | X | X | X | | | |
| Zinc 25 mg (2 capsules) once daily | | X | X | X | X | X | | | |
| Ask about AE and SAE | X | | | | X | | X | X | X |
| Vitals in-clinic$^f$ | | | | | | | X | X | X |
| Physical exam | | | | | | | X | X | X |
| EKG in-clinic | | | | | | | X | X | X |
| Swabs for RT-PCR | | | | | X | | X | | X |
| Bloodwork$^g$ | | | | | | | X | X | X |
| Review list of prior and concomitant medications | X | X | X | X | X | X | X | X | X |

Regarding Table 30: The antimicrobials include hydroxychloroquine 200 mg tablets (#20), azithromycin 250 mg tablets (#6), vitamin C 750 mg capsules (#80), vitamin D 750 IU capsules (#80), zinc 12.5 mg capsules (#80); the home health equipment includes an EKG (worn continuously), pulse oximeter, and thermometer; the pregnancy test is administered if the patient is a woman of childbearing potential; the patients are called at home to remind them to collect swabs for RT-PCT, ask about AE/SAE, ask about symptoms, and answer any questions; the vitals taken at home include an EKG, oxygen saturation, and temperature; the vitals in-clinic include height (only at first visit), weight, blood pressure (following 5 minutes sitting) pulse, respiratory rate, temperature, and oxygen saturation; and the bloodwork includes CBC, Complete Metabolic Panel, and CRP (details in section 9 Sample Collection).

Statistical Analysis: The treated patients in this study are compared to the placebo group. Measurements include PCR test results, presence or absence of symptoms, and symptom severity. PCR results will be compared between the groups as positive or negative In this study, the meaningful threshold is calculated as mean change in clinical symptoms as recorded in the diary, from Day 1 through week 12. Each category in the diary is assigned a number, 0 for None, 1 for Mild, 2 for Moderate and 3 for severe. Each category is analyzed independently and as a group. Ultimately, efficacy is determined based upon reduction and/or progression of symptomatic days, reduction of symptom severity, as well as analysis of the subject's RT-PCR testing per protocol. These data are compared to an existing database of de-identified Subject data.

The change of these measurements from the end to the baseline (post-pre) are used as the primary outcome, for example, $\mu e = \mu_{e1} - \mu_{e0}$, where $\mu_{e1}$ and $\mu_{e0}$ are the outcome of Subjects from the treatment group at the end and at baseline, respectively.

Categorical variables are summarized by presenting the number (n) and percent (%) of subjects in each category. All Statistical tests for the analysis are performed using the $p<0.05$ level of significance. All confidence intervals will be one-sided Sample size was calculated as follows:

$$n = \frac{\log \beta}{\log \rho}$$

Where $\beta$ = the probability of a Type II error
$\rho$ = the proportion of the population NOT affected
The proportion of the population affected by COVID-19 is 0.005 percent, thus 0.995 percent aren't affected The probability of a type II error is 0.05
Thus:

n=log 0.050 log 0.995 n=597.647

A sample size of 600 was used.

Example 5: Successful Treatment of COVID-19 Infected Outpatients and Prophylaxis of Immediate Associates Objective: to successfully treat COVID-19 infected outpatients and prophylaxis of immediate associates.

Procedure: Prospective COVID-19 infected individuals were diagnosed using a Pangea DNA/RNA Shield™ Collection Tube to obtain a nasopharyngeal swab and PCR +ve patients were entered into the study. They were immediately commenced on a 10 day course of Hydroxychloroquine (200 mg, twice a day, for 10 days), Azithromycin extended release (500 mg on day 1, then 250 mg a day for days 9-10), zinc (50 mg a day for days 1-10), Vitamin D (3000 IU a day for days 1-10) and Vitamin C (3000 mg a day for days 1-10). Some individuals lived alone, otherwise immediate partners and family deemed to be most exposed were given a prophylactic which comprised hydroxychloroquine 200 mg twice a day on day 1 only with Zinc, Vitamin C and Vitamin D for given at the same doses as above for days 1-10.

Results: In 11 families a total of 21 family members were identified to be PCR COVID-19 positive index cases and were treated with the above treatment protocol while 22 exposed associates with negative PCR were given the above prophylaxis protocol. This is shown below in Table 31. All 21 index cases were cured of COVID-19 infection as judged by the repeat swab PCR on day 10 and accompanying symptom resolution. None of the 22 highly exposed associates developed COVID-19 infection when retested on day 10 (day 14 in Family 10) in spite of close co-habitation with the infected index cases. TABLE 31: Results from families received 10-day course of daily HCQ (200 mg bd), AZ extended release (500 mg day 1, then 250 mg), zinc (50 mg), Vitamin D (3000 IU) and Vitamin C (3000 mg)

TABLE 31

| Family | Patientls treated | Age (years)- sex of the patient | Comorbidities of the patients | After treating with HAZDPAC Cured/ PCR test positive/negative/ other symptoms | After treating ZINCD+H family member prophylaxed |
|---|---|---|---|---|---|
| #1 | 1 | 23-male | Asthma | Negative PCR-day 10 | Parents overweight, diabetes, father with heart disease never got the disease |
| #2 | 3 | 60-male (father) 18-male (son) 16-female (daughter) | Asthma | All 3 patients cured | Mother didn't get the virus |
| #3 | 1 | 40-female | Arvoided intubation by leaving hospital | Sever multiple symptoms resolved at home | Husband did not turn positive |
| #4 | 2 | 78-male 77-female | BCG + COPD, diabetes, heart disease (heart surgery month prior Pacemaker, BCG | Both cured | Daughter, son-in-law and 2 grandkids didn't catch the virus |
| #5 | 3 | 56-male 27-male 24-female | Unable to eat or drink Asthma | Started treatment on day 10, Sever symptoms resolved Cured | Wife never got the disease |
| #6 | 1 | 56-female | | Admitted to hospital-sent home, as two kids were sick with fever. All recovered with vitamins | Husband never got the disease |
| #7 | 1 | 44-female | | Cured, autoimmune issues started | Husband and 4 kids never got the disease |
| #8 | 3 | 52-female 53-male 19-male | Lupus Severe asthma | Cured Cured Cured | Boyfriend (54 y) with Diabetes, son (18) and daughter (16) never got the disease |
| #9 | 2 | 45-female 16-male | | Both cured from severe symptoms of cough and fever | Husband and daughter never got the disease |
| #10 | 2 | 44-male 25-female 21-female | | Cured from loss of smell, fever, cough Cured Partially treated with HAZDPAC-slowly turned-ve | Mother (50 y) never got the disease |
| #11 | 1 | 33-female | No | ICU nurse recovered | Boyfriend never got the disease |

Apart from the families a further 11 single infected individuals found to be swab PCR positive were treated with the above treatment protocol. This is shown below in Table 32. All were also successfully cured of the infection.

TABLE 32

| Patient | Age (years)-sex of the patient | Comorbidities/symptoms of the patients | After treating with HAZDPAC Cured/not |
|---|---|---|---|
| #1 | 44-female (no BCG in childhood) | Asthma | Cured |
| #2 | 81-male | Diarrhea | Cured |
| #3 | 52-female | Fever | Cured |
| #4 | 66-male | Valve surgery | Cured |
| #5 | 29-female (no BCG in childhood) | Asthma | Cured |
| #6 | 50-female | Auto immune thyroiditis, sever cough and fever | Cured |
| #7 | 43-male | Cough, desaturation of oxygen | Cured |
| #8 | 53-male | Diarrhea, cough, fever, desaturation of oxygen | Cured |
| #9 | 44-female | Autoimmune history, fever, increase heart rate | Cured |
| #10 | 44-female | Pneumothorax discharged from ICU with COVID-19 | Cured |
| #11 | 43-male | Fever +ve Covid-19 PCR | Cured |

A further 9 individuals recently closely exposed to Covid-19 infected persons were given the prophylaxis protocol outlined above. The prophylactic worked very well with no exposed person acquiring the infection. This is shown in Table 33.

TABLE 33

| Individual | Age (years) & details of the individual | After treating with ZINCD+H |
|---|---|---|
| #1 | Mother of 16 year old child who had COVID-19 | Prophylaxed and never got the disease |
| #2 | 24-female, ICU nurse-multiple exposures | Prophylaxed and never got the disease |
| #3 | 47-male, cardiologist exposed to +ve patients | Prophylaxed and never got the disease |
| #4 | 70-male medical director of a hospital (exposed to numerous doctors with COVID-19) | Prophylaxed and never got the disease |
| #5 | 55-male anaesthesiologist (intubates COVID-19 patients) | Prophylaxed and never got the disease |
| #6 | 55-ICU nurse(worked on Covid-19 floor) | Prophylaxed and never got the disease |
| #7 | 40-ICU nurse many Covid-19 patients | Prophylaxed and never got the disease |
| #8 | 53-Doctor with pancreatitis | Prophylaxed and never got the disease |
| #9 | 28-Paramedic-healthy | Prophylaxed and never got the disease |

Discussion: It was demonstrated that a 10 day combination of hydroxychloroquine, azithromycin (for 5 days only), zinc with vitamin D and vitamin C, can result in uniform cure of COVID-19 infection when used in an outpatient population. The prophylaxis treatment noted above for those closely exposed to proven, infected patients can completely prevent spread of COVID-19. This combination of test-and-treat permits abolishing of new outbreaks of infection such as a 'next wave'—by avoiding quarantine to treat the infected and give prophylactics to surrounding staff and family.

In conclusion, this is an effective anti-Covid-19 therapy as well as an effective prophylactic combination capable of arresting the spread of coronavirus infection throughout the community. This is achieved by treating the index case and the surrounding associates of the patient as early as possible after infection is identified and then treating the people they live with and close associates.

Example 6: Presence of the SARS-CoV-2 by NGS of Fecal Samples

Objective: In view of the large percentage of SARS-CoV-2 detectible by RT-PCR in stools of infected patients, the objective was to identify the presence of the SARS-CoV-2 by NGS of fecal samples from symptomatic study participants positive for SARS-CoV-2 by nasopharyngeal sample RT-PCR, in addition to asymptomatic individuals (with or without prior nasopharyngeal sample RT-PCR). The objective was also to execute whole genome analysis to characterize SARS-CoV-2 mutational variations to identify potentially significant nucleotide changes.

Procedure: Study participants (n=14) underwent testing for SARS-CoV-2 from fecal samples by whole genome enrichment NGS. Following fecal collection (Zymo Research Shield Fecal Collection Tubes), RNA was extracted (Qiagen Allprep Power Viral Kit), reverse transcribed (New England Biolabs NEBNext 1st and 2nd Strand Synthesis Modules), library prepped (Illumina Nextera Flex for Enrichment), enriched (Ilumina Respiratory Virus Oligo Panel), and sequenced on Illumina's NextSeq 550 System. Sequences were then mapped to the SARS-CoV-2 Wuhan-Hu-1 (MN90847.3) complete genome utilizing One Codex's SARS-CoV-2 bioinformatics analysis pipeline. SARS-CoV-2 positive samples were further analyzed for mutational variants that differed from the reference genome. Of the 14 study participants, 12 also had their nasopharyngeal swabs tested for SARS-CoV-2 by RT-PCR.

Results: The results from patients that had their stool samples tested by whole genome enrichment NGS, and their nasopharyngeal swabs tested by RT-PCR for the presence of SARS-CoV-2 were evaluated. Of the 14 study participants, ten were symptomatic and tested positive for SARS-CoV-2 by RT-PCR, two asymptomatic individuals tested negative, and two other asymptomatic individuals did not undergo RT-PCR testing (Table 34). Patients 5 and 7, which tested positive by RT-PCR from nasopharyngeal swabs, were treated with the protocol from Example 5 above (Hydroxychloroquine, Azithromycin, vitamin C, vitamin D, and zinc for 10 days prior to fecal collection). Similarly, after positive nasopharyngeal swab, patient 13 was treated with vitamin C, vitamin D, and zinc for 10 days (the same protocol as noted above in Example 5) before fecal collection. The concordance of SARS-CoV-2 detection by enrichment NGS from stools among positive non-treated patients tested by RT-PCR nasopharyngeal analysis was 100% (7/7). Patient 8, who did not undergo nasopharyngeal analysis, tested positive for SARS-CoV-2 by NGS. The three patients (5, 7, 13) that received treatment prior to providing fecal samples, all tested negative by NGS. Asymptomatic patients 2 and 9, who tested negative by nasopharyngeal swab, were also negative by NGS, as was asymptomatic patient 14. Table 34 outlines the symptoms and SARS-CoV-2 testing results.

TABLE 34

| Sample ID | Symptoms | Nasopharyngeal Swab (RT-PCR) | Treated | Fecal (NGS) | Patient Location |
|---|---|---|---|---|---|
| Patient 1 | febrile, diarrhea, anosmia, O2 sat. <90% | + | no | + | PA |
| Patient 3 | febrile, diarrhea, O2 sat. <90% | + | no | + | CA |
| Patient 4 | febrile, diarrhea, anosmia, O2 sat. <90% | + | no | + | AZ |
| Patient 6 | febrile, cough, anosmia | + | no | + | AZ |
| Patient 8 | none | n/a | no | + | CA |
| Patient 10 | febrile, cough, headache | + | 00 | + | GA |
| Patient 11 | febrile, cough, headache | + | 00 | + | GA |
| Patient 12 | febrile, cough | + | 00 | + | GA |
| Patient 5 | febrile, cough | + | yes | − | CA |
| Patient 7 | febrile, cough | + | yes | − | GA |
| Patient 13 | febrile, cough | + | yes | − | GA |
| Patient 2 | none | − | no | − | CA |
| Patient 9 | none | − | no | − | CA |
| Patient 14 | none | n/a | no | − | CA |

All fecal samples analyzed by enrichment NGS from positive patients by RT-PCR, achieved 100% genome coverage of SARS-CoV-2 except for patient 3 which had 45%, and patient 10 which had 93% coverage. Table 35 outlines the enrichment NGS metrics.

TABLE 35

| Sample ID | Genome Coverage | # Variants (over 10×) | Mapped Reads | Mean Depth |
|---|---|---|---|---|
| Patient 1 | 100% | 11 | 465645 | 1129.8× |
| Patient 3 | 45% | 11 | 5984 | 31.7× |
| Patient 4 | 100% | 9 | 131582 | 318.6× |
| Patient 6 | 100% | 10 | 793603 | 1924.6× |
| Patient 8 | 100% | 10 | 496852 | 1206.7 |
| Patient 10 | 93% | 9 | 5929 | 15.6× |
| Patient 11 | 100% | 10 | 1270734 | 3075.3× |
| Patient 12 | 100% | 10 | 38256 | 92.7× |

The total number of SARS-CoV-2 mapped reads for patients 1, 3, 4, 6, 8, 10, 11, and 12 were 465645, 5984, 131582, 793603, 496852, 5929, 1270734, and 38256 respectively. The mean read depths of SARS-CoV-2 for patients 1, 3, 4, 6, 8, 10, 11, and 12 were 1129.8×, 31.7×, 318.6×, 1924.6×, 1206.7×, 15.5×, 3075.3×, and 92.7×, and respectively. The read depths at specific coordinates along the SARS-CoV-2 genome for each patient are captured in FIGS. 3A-3H. Whole genome alignment of SARS-CoV-2 in patients 1, 3, 4, 6, 8, 10, 11, and 12 (respectively) as identified by One Codex's SARS-CoV-2 analysis pipeline. The x-axis depicts the genomic coordinates as aligned to the MN908947.3 reference genome, and the y-axis represents the read depth at specific loci.

Following alignment and mapping of SARS-CoV-2, patient genomes were compared to the Wuhan-Hu-1 (MN90847.3) SARS-CoV-2 reference genome via One Codex's bioinformatics pipeline to identify mutational variations. This analysis identified nucleotide variants at positions nt241 (C→T) and nt23403 (A→G) across all positive patients, and variants at positions nt3037 (C→T) and nt25563 (G→T) in seven of the eight patients (Table 3). Interestingly, patients 8, 11, and 12 harbored the same set of variants, as did patients 4 and 6 (who were kindred). Unique variants not identified in any of the other individuals were detected in patients 1, 3, 6, and 10, with patient 3 harboring the most distinct SARS-CoV-2 genome with eight unique variants, followed by patient 1 with seven. Collectively, there were thirty-three different mutations among the patients in which SARS-CoV-2 was detected by whole genome enrichment NGS. Table 36 outlines the SARS-CoV-2 genomic positions, variant changes, and frequencies across the positive patient cohort.

TABLE 36

| Region (ORF) | Position | Variant | Patient 1 | Patient 3 | Patient 4 | Patient 6 | Patient 8 | Patient 10 | Patient 11 | Patient 12 |
|---|---|---|---|---|---|---|---|---|---|---|
| 5'-UTR | 241 | C → T | 100% | 100% | 100% | 100% | 100% | 100% | 100% | 100% |
| 1a | 833 | T → C | x | x | x | x | 100% | x | 100% | 100% |
| 1a | 1059 | C → T | x | x | 100% | 100% | 99% | 100% | 100% | 100% |
| 1a | 1758 | C → T | x | x | 100% | 100% | x | x | x | x |
| 1a | 1973 | C → T | x | x | x | 87% | x | x | x | x |
| 1a | 3037 | C → T | 100% | X | 100% | 100% | 100% | 100% | 100% | 100% |
| 1a | 3078 | C → T | x | 89% | x | x | x | x | x | x |
| 1a | 4866 | G → T | 75% | x | x | x | x | x | x | x |
| 1a | 6720 | C → T | 93% | x | x | x | x | x | x | x |
| 1a | 8102 | G → T | x | 100% | x | x | x | x | x | x |
| 1a | 9401 | T → C | x | x | x | x | x | 64% | x | x |
| 1a | 9403 | T → A | x | x | x | x | x | 64% | x | x |
| 1a | 10870 | G → T | x | x | 100% | 100% | x | x | x | x |

TABLE 36-continued

| Region (ORF) | Position | Variant | Patient 1 | Patient 3 | Patient 4 | Patient 6 | Patient 8 | Patient 10 | Patient 11 | Patient 12 |
|---|---|---|---|---|---|---|---|---|---|---|
| 1a | 11123 | G → A | x | x | 100% | 100% | x | x | x | x |
| 1b | 14408 | C → T | 100% | x | 100% | 100% | 100% | x | 100% | 100% |
| 1b | 14877 | C → T | x | 100% | x | x | x | x | x | x |
| 1b | 16616 | C → T | x | x | x | x | 100% | x | 100% | 100% |
| 1b | 16848 | C → T | 100% | x | x | x | x | x | x | x |
| 1b | 18652 | C → A | x | x | x | x | x | 83% | x | x |
| 1b | 19989 | T → G | x | 100% | x | x | x | x | x | x |
| Spike | 21576 | T → G | x | 83% | x | x | x | x | x | x |
| Spike | 23264 | G → A | x | 75% | x | x | x | x | x | x |
| Spike | 23403 | A → G | 100% | 100% | 100% | 100% | 100% | 100% | 100% | 100% |
| Spike | 23603 | C → T | 82% | x | x | x | x | x | x | x |
| 3a | 25563 | G → T | x | 100% | 100% | 100% | 100% | 100% | 100% | 100% |
| 3a | 25976 | C → A | x | x | x | x | 100% | x | 100% | 100% |
| 8 | 27964 | C → T | x | x | x | x | 100% | x | 100% | 100% |
| Nucleoprotein | 28881 | G → A | 100% | x | x | x | x | x | x | x |
| Nucleoprotein | 28882 | G → A | 100% | x | x | x | x | x | x | x |
| Nucleoprotein | 28883 | G → C | 100% | x | x | x | x | x | x | x |
| Nucleoprotein | 28997 | C → T | x | 100% | x | x | x | x | x | x |
| Nucleoprotein | 29019 | A → T | x | 100% | x | x | x | x | x | x |
| Nucleoprotein | 29364 | C → G | x | x | x | x | x | 85% | x | x |

Discussion: Although previous studies have identified SARS-CoV-2 in fecal collections by RT-PCR, this study was able to report whole genome sequencing (WGS) of SARS-CoV-2 from stool samples. SARS-CoV-2 was identified in patients that tested positive by nasopharyngeal swab RT-PCR analysis and unique genomes in 62.5% of the NGS positive patients was observed. The overall homology among the genomes was high (99.97%), with variations identified in the ORF regions 1a, 1b, S, 3a, 8, and N. Of particular interest, was the adenine to guanine change in the S protein at position nt23403 which converts aspartic acid to glycine (D→G).

Conclusion: Next generation sequencing identified the SARS-CoV-2 whole genome sequence in 100% of patients with positive nasopharyngeal RT-PCR and did not detect it in treated patients, or those with negative rt-PCR. These results highlight the importance of metagenomic analysis of the SARS-CoV-2 viral genome.

Example 7: Randomized, Double-Blind, Placebo-Controlled Phase IIA Study of Hydroxychloroquine, Vitamin C, Vitamin D, and Zinc for the Prevention of COVID-19 Infection Objectives: Prevention of COVID-19, Lack of COVID-19 symptoms, and assessment of safety and tolerability Procedure: Screening Period (Days −7 to −1): Prescription of home health monitoring equipment that includes a thermometer, a pregnancy test if applicable, and a daily diary. There are two groups being studied: Arm 1 and Arm 2.

Arm 1 is prescribed the following antimicrobials: hydroxychloroquine 200 mg twice a day for 1 day only, vitamin C 3000 IU per day for 12 weeks, vitamin D 3000 IU per day for 12 weeks, and zinc 50 mg per day for 12 weeks. The zinc can be reduced to 25 mg if GI upset occurs. The hydroxychloroquine is to be taken first thing in the morning as soon as subject has eaten and again right before bed, and must be separated from vitamin dose by at least 2 hours.

Arm 2 is prescribed the following antimicrobials: Placebo twice a day for 1 day only, vitamin C 3000 IU per day for 12 weeks, vitamin D 3000 IU per day for 12 weeks, and zinc 50 mg per day for 12 weeks. The zinc can be reduced to 25 mg if GI upset occurs.

Day 1: Patient is called to teach them how to use the diary in the EDC, discuss the medication regimen, and answer any questions they may have. Patient takes pregnancy test if applicable, collects a temperature reading, completes their diary, and takes the prescribed treatment regimen. Table 37 outlines the prescribed treatment regimen for Day 1.

TABLE 37

| Drug | AM Dose | PM Dose |
|---|---|---|
| Hydroxychloroquine (or placebo) | 200 mg | 200 mg |
| Vitamin C | 1500 mg | 1500 mg |
| Vitamin D | 1500 IU | 1500 IU |
| Zinc | 25 mg | 25 mg |

Day 2: Patient collects a temperature reading, completes their diary, and is called on the phone for assessment of any adverse events or serious adverse events, assessment of any COVID-19 symptoms, the list of prior and concomitant medications is updated, any questions the patient has are answered, and the patient takes their prescribed treatment regimen. Table 38 outlines the prescribed treatment regimen for Day 2.

TABLE 38

| Drug | AM Dose | PM Dose |
|---|---|---|
| Vitamin C | 1500 mg | 1500 mg |
| Vitamin D | 1500 IU | 1500 IU |
| Zinc | 25 mg | 25 mg |

Days 3-10: Patient collects a temperature reading, completes their diary, and takes their prescribed treatment regimen. Table 8 outlines the prescribed treatment regimen for Days 3-10.

TABLE 8

| Drug | AM Dose | PM Dose |
|---|---|---|
| Vitamin C | 1500 mg | 1500 mg |
| Vitamin D | 1500 IU | 1500 IU |
| Zinc | 25 mg | 25 mg |

Day 14: The patient is called for instruction on how to collect a nasal swab and package for shipping, assessment COVID-19 symptoms, updating their list of prior and concomitant medications, and answering any questions they may have.

Week 3: The patient is called for assessment of any adverse events or serious adverse events, assessment of any COVID-19 symptoms, updating their list of prior and concomitant medications, and answering any questions they may have. The patient takes a temperature reading, completes their diary, and takes the prescribed treatment regimen.

Table 39 outlines the treatment regime for week 3.

TABLE 39

| Drug | AM Dose | PM Dose |
| --- | --- | --- |
| Vitamin C | 1500 mg | 1500 mg |
| Vitamin D | 1500 IU | 1500 IU |
| Zinc | 25 mg | 25 mg |

Week 4: The patient is called for assessment of any adverse events or serious adverse events, assessment of any COVID-19 symptoms, updating their list of prior and concomitant medications, and answering any questions they may have. The patient takes a temperature reading, completes their diary, and takes the prescribed treatment regimen. The patient also collects a nasal swab.

Table 40 outlines the treatment regime for week 4.

TABLE 40

| Drug | AM Dose | PM Dose |
| --- | --- | --- |
| Vitamin C | 1500 mg | 1500 mg |
| Vitamin D | 1500 IU | 1500 IU |
| Zinc | 25 mg | 25 mg |

Weeks 5-11: The patient is called weekly for assessment of any adverse events or serious adverse events, assessment of any COVID-19 symptoms, updating their list of prior and concomitant medications, and answering any questions they may have. The patient takes a weekly temperature reading, completes their diary, and takes the prescribed treatment regimen.

Table 41 outlines the treatment regime for weeks 5-11.

TABLE 41

| Drug | AM Dose | PM Dose |
| --- | --- | --- |
| Vitamin C | 1500 mg | 1500 mg |
| Vitamin D | 1500 IU | 1500 IU |
| Zinc | 25 mg | 25 mg |

Week 12: The patient presents to the clinic (or video conference) for evaluation that includes assessment for adverse events and serious adverse events, updating their list of prior and concomitant medications, a physical exam, nasal swab collection and COVID-19 sample collection.

Samples for COVID-19 testing are collected using synthetic swabs with plastic shafts. Nasal swabs are collected and immediately placed into a sterile vial with 2-3 mL of viral transport media. The vials are placed into biohazard bags, boxed up, the box sterilized, and picked up for shipment to the central laboratory. Samples are tested by RT-PCR.

Table 42 presents the schedule of events for Example 7.

TABLE 42

| Assessment | Screening (Day −7 to Day 1) | Day 1 | Day 2 | Day 3-10 | Day 14 | Week 3 | Week 4/ Month 1 | Week 5 |
| --- | --- | --- | --- | --- | --- | --- | --- | --- |
| Informed Consent & Demographics | X | | | | | | | |
| Initial Review of Prior and Concomitant Medications | X | | | | | | | |
| Medical Records review, including baseline EKG | X | | | | | | | |
| Randomization | X | | | | | | | |
| Prescription of Hydroxychloroquine or placebo, vitamin C, vitamin D, and zinc | X | | | | | | | |
| Provision of daily diary, thermometer and pregnancy test | X | | | | | | | |
| Pregnancy Test if applicable | | X | | | | | | |
| Temperature at home | | X | X | X | X | X | X | X |
| Complete daily diary | | X | X | X | X | X | X | X |
| Hydroxychloroquine 200 mg | | X | | | | | | |
| Vitamin C 3000 mg | | X | X | X | X | X | X | X |
| Vitamin D 3000 IU | | X | X | X | X | X | X | X |
| Zinc 50 mg[a] | | X | X | X | X | X | X | X |
| Phone/video call to patient[b] | X | X | X | | X | X | X | X |
| Update list of prior and concomitant medications | | X | X | X | X | X | X | X |
| Ask about AE and SAE | | X | X | X | X | X | X | X |
| Assessment of COVID-19 symptoms | | X | X | X | X | X | X | X |
| Swabs for RT-PCR | | X | | | X | | X | |
| Vitals in-clinic[c] | | | | | | | | |
| Physical Exam | | | | | | | | |

| Assessment | Week 6 | Week 7 | Week 8/ Month 2 | Week 9 | Week 10 | Week 11 | Week 12/ Month 3 |
| --- | --- | --- | --- | --- | --- | --- | --- |
| Informed Consent & Demographics | | | | | | | |
| Initial Review of Prior and Concomitant Medications | | | | | | | |
| Medical Records review, including baseline EKG | | | | | | | |
| Randomization | | | | | | | |
| Prescription of Hydroxychloroquine or placebo, vitamin C, vitamin D, and zinc | | | | | | | |

TABLE 42-continued

| | | | | | | | |
|---|---|---|---|---|---|---|---|
| Provision of daily diary, thermometer and pregnancy test | | | | | | | |
| Pregnancy Test if applicable | | | | | | | |
| Temperature at home | X | X | X | X | X | X | X |
| Complete daily diary | X | X | X | X | X | X | X |
| Hydroxychloroquine 200 mg | | | | | | | |
| Vitamin C 3000 mg | X | X | X | X | X | X | X |
| Vitamin D 3000 IU | X | X | X | X | X | X | X |
| Zinc 50 mg[a] | X | X | X | X | X | X | X |
| Phone/video call to patient[b] | X | X | X | X | X | X | |
| Update list of prior and concomitant medications | X | X | X | X | X | X | X |
| Ask about AE and SAE | X | X | X | X | X | X | X |
| Assessment of COVID-19 symptoms | X | X | X | X | X | X | X |
| Swabs for RT-PCR | | | | | | | X |
| Vitals in-clinic[c] | | | | | | | X |
| Physical Exam | | | | | | | X |

Regarding Table 42: The Zinc may be reduced to 25 mg if GI upset occurs, phone/video calls to the patient occur weekly during Weeks 2-11, and vitals in-clinic include height, weight, blood pressure (following 5 minutes sitting) pulse, respiratory rate, temperature, and oxygen saturation.

Statistical Analysis: The treated patients in this study are compared to the placebo group. Measurements include PCR test results, presence or absence of symptoms, and symptom severity.

The change of these measurements from the end to the baseline (post-pre) are used as the primary outcome, for example, $\mu e = \mu e1 - \mu e0$, where $\mu e1$ and $\mu e0$ are the outcome of patients from the treatment group at the end and at baseline, respectively.

$H_0$: $\Delta \leq \delta_0$ against $H_\alpha$: $\Delta > \delta_0$ where $\delta_0$ is a clinically meaningful threshold to measure the disease symptoms. In this study, that meaningful threshold is calculated as mean change in clinical symptoms as recorded in the diary, from baseline through week 12. Each category in the diary is assigned a number, 0 for None, 1 for Mild, 2 for Moderate and 3 for severe. Each category is analyzed independently and as a group.

Categorical variables are summarized by presenting the number (n) and percent (%) of subjects in each category. All Statistical tests for the analysis are performed using the $p<0.05$ level of significance. All confidence intervals are one-sided.

Since these are healthcare workers who are exposed to COVID-19 at every shift, efficacy is determined by RT-PCR testing, as well as the presence or absence of symptoms as recorded in the patient diary via EDC.

Having thus described the invention, it should be apparent that numerous structural modifications and adaptations may be resorted to without departing from the scope and fair meaning of the instant invention as set forth herein above and described herein below by the claims.

While particular forms of the invention have been illustrated and described, it will also be apparent to those skilled in the art that various modifications can be made without departing from the spirit and scope of the invention.

Although the present invention has been described in considerable detail with reference to certain preferred embodiments, other embodiments are possible. The forgoing description is not intended to be exhaustive or to limit the invention to the precise form disclosed. Many modifications and variations are possible in light of the above teaching. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments/methods contained in this disclosure. All references cited herein are incorporated by reference. Insofar as the description above and the accompanying drawings disclose any additional subject matter that is not within the scope of the claims below, the inventions are not dedicated to the public and the right to file one or more applications to claim such additional inventions is reserved.

What is claimed is:

1. A composition for treating COVID-19 infection in an individual, the composition consisting of:
   a) hydroxychloroquine;
   b) azithromycin;
   c) vitamin C;
   d) 40,000 IU to 100,000 IU of vitamin D; and
   e) zinc.

2. The composition of claim 1, wherein the composition consists of:
   a) 200 mg to 1,000 mg of hydroxychloroquine;
   b) 250 mg to 500 mg of azithromycin;
   c) 1,000 mg to 10,000 mg of vitamin C;
   d) 40,000 IU to 100,000 IU of vitamin D; and
   e) 25 mg to 75 mg of zinc.

3. The composition of claim 1, wherein the composition consists of:
   a) 200 mg of hydroxychloroquine;
   b) 500 mg of azithromycin;
   c) 3,000 mg of vitamin C;
   d) 40,000 IU to 100,000 IU of vitamin D; and
   e) 50 mg of zinc.

4. The composition of claim 1, wherein the composition consists of:
   a) 200 mg of hydroxychloroquine;
   b) 250 mg of azithromycin;
   c) 3,000 mg of vitamin C;
   d) 40,000 IU to 100,000 IU of vitamin D; and
   e) 50 mg of zinc.

5. The composition of claim 1, wherein the composition consists of:
   a) 20 mg to 2,000 mg of hydroxychloroquine;
   b) 250 mg to 500 mg of azithromycin;
   c) 250 mg to 10,000 mg of vitamin C;
   d) 40,000 IU to 100,000 IU of vitamin D; and
   e) 5 mg to 100 mg of zinc.

6. The composition of claim 1, wherein the composition consists of:
   a) 50 mg to 200 mg of hydroxychloroquine;
   b) 250 mg to 500 mg of azithromycin;
   c) 1500 mg to 3000 mg of vitamin C;
   d) 40,000 IU to 100,000 IU of vitamin D; and
   e) 25 mg to 75 mg of zinc.

7. A composition for treating COVID-19 infection in an individual, the composition consisting of:
 a) hydroxychloroquine;
 b) vitamin C;
 c) 40,000 IU to 100,000 IU of vitamin D; and
 d) zinc.

8. The composition of claim 7, wherein the composition consists of:
 a) 200 mg to 1,000 mg of hydroxychloroquine;
 b) 1,000 mg to 10,000 mg of vitamin C;
 c) 40,000 IU to 100,000 IU of vitamin D; and
 d) 25 mg to 75 mg of zinc.

9. The composition of claim 7, wherein the composition consists of:
 a) 200 mg of hydroxychloroquine;
 b) 3,000 mg of vitamin C;
 c) 40,000 IU to 100,000 IU of vitamin D; and
 d) 50 mg of zinc.

10. The composition of claim 7, wherein the composition consists of:
 a) 400 mg of hydroxychloroquine;
 b) 3,000 mg of vitamin C;
 c) 40,000 IU to 100,000 IU of vitamin D; and
 d) 50 mg of zinc.

11. The composition of claim 7, wherein the composition consists of:
 a) 20 mg to 2,000 mg of hydroxychloroquine;
 b) 250 mg to 10,000 mg of vitamin C;
 c) 40,000 IU to 100,000 IU of vitamin D; and
 d) 5 mg to 100 mg of zinc.

12. The composition of claim 7, wherein the composition consists of:
 a) 50 mg to 1,000 mg of hydroxychloroquine;
 b) 250 mg to 3,000 mg of vitamin C;
 c) 40,000 IU to 100,000 IU of vitamin D; and
 d) 12.5 mg to 100 mg of zinc.

13. The composition of claim 7, wherein the composition consists of:
 a) 200 mg to 1,000 mg of hydroxychloroquine;
 b) 1500 mg to 3,000 mg of vitamin C;
 c) 40,000 IU to 100,000 IU of vitamin D; and
 d) 25 mg to 75 mg of zinc.

14. A composition for treating COVID-19 infection in an individual, the composition consisting of:
 a) hydroxychloroquine;
 b) doxycycline;
 c) vitamin C;
 d) 40,000 IU to 100,000 IU vitamin D; and
 e) zinc.

15. The composition of claim 14, wherein the composition consists of:
 a) 20 mg to 2,000 mg of hydroxychloroquine;
 b) 25 mg to 800 mg of doxycycline;
 c) 50 mg to 10,000 mg of vitamin C;
 d) 40,000 IU to 100,000 IU of vitamin D; and
 e) 5 mg to 100 mg of zinc.

16. The composition of claim 14, wherein the composition consists of:
 a) 200 mg to 1,000 mg of hydroxychloroquine;
 b) 25 mg to 800 mg of doxycycline;
 c) 1,000 mg to 10,000 mg of vitamin C;
 d) 40,000 IU to 100,000 IU of vitamin D; and
 e) 25 mg to 75 mg of zinc.

17. The composition of claim 14, wherein the composition consists of:
 a) 50 mg to 200 mg of hydroxychloroquine;
 b) 25 mg to 800 mg of doxycycline;
 c) 1500 mg to 3000 mg of vitamin C;
 d) 40,000 IU to 100,000 IU of vitamin D; and
 e) 25 mg to 75 mg of zinc.

18. The composition of claim 14, wherein the composition consists of:
 a) 200 mg of hydroxychloroquine;
 b) 25 mg to 800 mg of doxycycline;
 c) 3,000 mg of vitamin C;
 d) 40,000 IU to 100,000 IU of vitamin D; and
 e) 50 mg of zinc.

19. The composition of claim 14, wherein the composition consists of:
 a) 400 mg of hydroxychloroquine;
 b) 25 mg to 800 mg of doxycycline;
 c) 3,000 mg of vitamin C;
 d) 40,000 IU to 100,000 IU of vitamin D; and
 e) 50 mg of zinc.

20. The composition of claim 14, wherein the composition consists of:
 a) 200 mg of hydroxychloroquine;
 b) 25 mg to 800 mg of doxycycline;
 c) 1500 mg of vitamin C;
 d) 40,000 IU to 100,000 IU of vitamin D; and
 e) 50 mg of zinc.

21. The composition of claim 14, wherein the composition consists of:
 a) 400 mg of hydroxychloroquine;
 b) 25 mg to 800 mg of doxycycline;
 c) 1500 mg of vitamin C;
 d) 40,000 IU to 100,000 IU of vitamin D; and
 e) 50 mg of zinc.

* * * * *